(12) United States Patent
Fu

(10) Patent No.: US 9,922,291 B2
(45) Date of Patent: Mar. 20, 2018

(54) INTELLIGENT APPARATUS FOR PROVIDING PERSONALIZED CONFIGURATION OF WHEELCHAIR TILT AND RECLINE

(71) Applicant: UNIVERSITY OF CENTRAL OKLAHOMA, Edmond, OK (US)

(72) Inventor: Jicheng Fu, Edmond, OK (US)

(73) Assignee: University of Central Oklahoma, Edmond, OK (US)

( * ) Notice: Subject to any disclaimer, the term of this patent is extended or adjusted under 35 U.S.C. 154(b) by 212 days.

(21) Appl. No.: 14/632,198

(22) Filed: Feb. 26, 2015

(65) Prior Publication Data
US 2015/0170058 A1    Jun. 18, 2015

Related U.S. Application Data

(63) Continuation of application No. 14/304,758, filed on Jun. 13, 2014, now Pat. No. 8,996,432.

(60) Provisional application No. 61/891,600, filed on Oct. 16, 2013.

(51) Int. Cl.
| | |
|---|---|
| G06N 99/00 | (2010.01) |
| A61G 5/10 | (2006.01) |
| G06F 17/50 | (2006.01) |
| G06F 19/00 | (2018.01) |
| G06N 3/10 | (2006.01) |
| A61G 7/057 | (2006.01) |

(52) U.S. Cl.
CPC ......... *G06N 99/005* (2013.01); *A61G 5/1056* (2013.01); *G06F 17/5009* (2013.01); *G06F 19/345* (2013.01); *A61G 5/1067* (2013.01); *A61G 5/1075* (2013.01); *A61G 7/057* (2013.01); *A61G 2203/10* (2013.01); *G06N 3/10* (2013.01)

(58) Field of Classification Search
None
See application file for complete search history.

(56) References Cited

U.S. PATENT DOCUMENTS

| | | | |
|---|---|---|---|
| 7,246,856 B2 | 7/2007 | Kruse et al. | |
| 2007/0050111 A1* | 3/2007 | Mattes | A61G 5/04 701/36 |
| 2008/0097256 A1* | 4/2008 | Torres | A61G 5/045 601/24 |

(Continued)

OTHER PUBLICATIONS

R. Aissaoui, C. Kauffmann, J. Dansereau, and J. A. de Guise, "Analysis of pressure distribution at the body-seat interface in able-bodied and paraplegic subjects using a deformable active contour algorithm," Med Eng Phys, vol. 23, pp. 359-367, Jul. 2001.

(Continued)

*Primary Examiner* — Kakali Chaki
*Assistant Examiner* — Daniel Pellett
(74) *Attorney, Agent, or Firm* — Berenato & White, LLC

(57) ABSTRACT

A method and apparatus for providing personalized configuration of physical supports for the human body, comprising accepting input including an individual's demographic information, neurological attributes, physical history, operational environment, and outcome or use objectives, processing user input employing an artificial intelligence engine, and then returning guidance and/or control parameters directed to seating adjustment and positioning, including incline angles for wheelchair tilt and recline.

19 Claims, 27 Drawing Sheets

(56) References Cited

U.S. PATENT DOCUMENTS

2010/0280629 A1 11/2010 Jung et al.
2014/0107493 A1 4/2014 Yuen et al.

OTHER PUBLICATIONS

Y. K. Jan, F. Liao, M. A. Jones, L. A. Rice, and T. Tisdell, "Effect of durations of wheelchair tilt-in-space and recline on skin perfusion over the ischial tuberosity in people with spinal cord injury," Arch Phys Med Rehabil, vol. 94, pp. 667-672, Apr. 2013.
Y. K. Jan, M. A. Jones, M. H. Rabadi, R. D. Foreman, and A. Thiessen, "Effect of wheelchair tilt-in-space and recline angles on skin perfusion over the ischial tuberosity in people with spinal cord injury," Archives of physical medicine and rehabilitation, vol. 91, pp. 1758-1764, Nov. 2010.
Permobil. (2014). Virtual Seating Coach. Available: http://www.permobilus.com/virtualseatingcoach.php.
D. W. Byrne and C. A. Salzberg, "Major risk factors for pressure ulcers in the spinal cord disabled: a literature review," Spinal Cord, vol. 34, pp. 255-263, May 1996.
M. Makhsous, M. Priebe, J. Bankard, D. Rowles, M. Zeigler, D. Chen, and F. Lin, "Measuring tissue perfusion during pressure relief maneuvers: insights into preventing pressure ulcers," The journal of spinal cord medicine, vol. 30, pp. 497-507, 2007.
Gélis A., Dupeyron A., Legros P., Benaïm, C., Pelissier J., and Fattal4 C., "Pressure ulcer risk factors in persons with spinal cord injury Part 2: the chronic stage", Spinal Cord (2009) 47, 651-661.
M. Reddy, S. S. Gill, and P. A. Rochon, "Preventing pressure ulcers: a systematic review," JAMA : the journal of the American Medical Association, vol. 296, pp. 974-984, Aug. 23, 2006.
B. E. Dicianno, et al., "RESNA position on the application of tilt, recline, and elevating legrests for wheelchairs," Assist Technol, vol. 21, pp. 13-22; quiz 24, Spring 2009.
S. E. Sonenblum and S. H. Sprigle, "The impact of tilting on blood flow and localized tissue loading," J Tissue Viability, vol. 20, pp. 3-13, Feb. 2011.
Y.K. Wu, H.Y. Liu, J. Brown, A. Kelleher, H. Wang, R. A. Cooper, "A Smartphone Application for Improving Powered Seat Functions Usage: A Preliminary Test", RESNA Annual Conference—2013.

S. V. Hiremath, D. Ding, and R. A. Cooper, "Development and evaluation of a gyroscope-based wheel rotation monitor for manual wheelchair users," J Spinal Cord Med, vol. 36, pp. 347-356, Jul. 2013.
J. Nixon, G. Cranny, and S. Bond, "Pathology, diagnosis, and classification of pressure ulcers: comparing clinical and imaging techniques," Wound repair and regeneration : official publication of the Wound Healing Society [and] the European Tissue Repair Society, vol. 13, pp. 365-372, Jul.-Aug. 2005.
F. Liao, S. Burns, and Y.-K. Jan, "Skin blood flow dynamics and its role in pressure ulcers," Journal of Tissue Viability, vol. 22, pp. 25-36, 2013.
Y. K. Jan and M. B. David, "Technology for Pressure Ulcer Prevention," Topics in Spinal Cord Injury Rehabilitation, vol. 11, pp. 30-41, 2006.
Fu, Jicheng, et al. "Capturing and analyzing wheelchair maneuvering patterns with mobile cloud computing." Engineering in Medicine and Biology Society (EMBC), 2013 35th Annual International Conference of the IEEE. IEEE, 2013.
Fu, Jicheng, Yih-Kuen Jan, and Maria Jones. "Development of intelligent model to determine favorable wheelchair tilt and recline angles for people with spinal cord injury." Engineering in Medicine and Biology Society, EMBC, 2011 Annual International Conference of the IEEE. IEEE, 2011.
Barea, Rafael, et al. "EOG guidance of a wheelchair using spiking neural networks." ESANN. 2000.
Liu, Hsin-Yi, et al. "Seating virtual coach: A smart reminder for power seat function usage." Technology and Disability 22.1 (2010): 53-60.
Fu, Jicheng, et al. "Towards an intelligent system for clinical guidance on wheelchair tilt and recline usage." Engineering in Medicine and Biology Society (EMBC), 2012 Annual International Conference of the IEEE. IEEE, 2012.
Fu, Jicheng, et al. "Using Artificial Neural Network to Determine Favorable Wheelchair Tilt and Recline Usage in People with Spinal Cord Injury: Training ANN with Genetic Algorithm to Improve Generalization." Tools with Artificial Intelligence (ICTAI), 2011 23rd IEEE International Conference on. IEEE, 2011.

* cited by examiner

INTELLIGENT APPARATUS FOR PROVIDING PERSONALIZED CONFIGURATION OF WHEELCHAIR TILT AND RECLINE

CROSS REFERENCES TO RELATED APPLICATIONS

This application is a continuation of U.S. patent application Ser. No. 14/304,758 filed on Jun. 13, 2014, entitled "Intelligent apparatus for providing personalized configuration of wheelchair tilt and recline". This application is based on and also claims the benefit of U.S. Provisional Patent Application No. 61/891,600 filed on Oct. 16, 2013 in the name of Jicheng Fu, which is expressly incorporated herein by reference in its entirety.

STATEMENT AS TO RIGHTS TO INVENTIONS MADE UNDER FEDERALLY SPONSORED RESEARCH OR DEVELOPMENT

This invention was made with government support under Grant Number 8P20GM103447 awarded by the National Institute of Health. The government has certain rights in the invention.

FIELD OF THE INVENTION

The present invention relates to providing personalized configuration of physical supports for the human body. More particularly, the present invention relates to optimization of physical supports and human positioning to achieve a desired outcome, including reducing the risk of pressure ulcers in general, and reducing the risk of pressure ulcers for people with spinal cord injury (SCI).

REFERENCE TO COMPUTER PROGRAM LISTING APPENDICES ON CD-R

This application includes herewith a transmittal under 37 C.F.R § 1.52(e) of a Computer Program Listing Appendix on Compact Disk (CD), where the transmittal comprises duplicate compact discs (CDs), totaling two (2) CDs, respectively labeled "Copy 1" and "Copy 2". Each disk contains the same files. The discs are IBM-PC machine formatted and MICROSOFT WINDOWS Operating System compatible, and include identical copies of the following list of two (2) files, where each file has been saved as a document viewable using MICROSOFT WORD. All of the materials on the compact disk, including the computer program listings contained in the following two (2) files, are incorporated herein by reference in their entirety. The two files are: APPENDIX A—Listing 1 Mobile (61,440 bytes) and APPENDIX B—Listing 2 Mobile-Cloud (366,592 bytes). The referenced listings were created on May 6, 2014.

The Table of Contents for APPENDIX A—Listing 1 Mobile is as follows:
Contents
  ClsTrainer
  Fragment AngleMeter
  Fragment Form
  FragmentFrequency
  FragmentList
  Fragment Result
  InitActivity
  InputData
  Main
  ResultTask
  TtsIntentService The Table of Contents for APPENDIX B—Listing 2 Mobile-Cloud is as follows:
Contents
  App Engine Source Code (Cloud)
    AngleData
    ApplicationUser.java
    BloodFlowCore.java
    BloodFlowResult.java
    DataManager
    EMF
    LinearUnit.java
    MLP.java
    NeuralConnection.java
    Range.java
    ResultEndpoint.java
    UserEndpoint.java
  App Engine Servlets (Cloud)
    CheckAnglesServlet.java
    DeletcUscrScrvlet.java
    SignInServlet.java
    SignOutServlet.java
    UpdateUserServlet.java
  Google App Engine JSP/html Pages (Web)
    admin.jsp
    check.jsp
    duration.jsp
    editUser.jsp
    index.html
    optimal.jsp
    profile.jsp
    results.jsp
    welcome.jsp
  Android Source Code (Mobile)
    CloudEndpointUtils.java
    Datastore.java
    FragmentAngleAdjustment.java
    FragmentAngleMeter
    FragmentCheck.java
    FragmentForm.java
    FragmentFrequency.java
    FragmentList.java
    FragmentOptimal.java
    FragmentResult.java
    LoginActivity.java
    MenuActivity.java

BACKGROUND OF THE INVENTION

Negative physiological conditions (e.g., attention deficit, lower back pain, pressure ulcers) may be experienced by people who are seated for long periods of time (e.g., long-haul truck drivers, airline pilots). Pressure ulcers are often experienced by people having compromised mobility (e.g., the elderly and infirm). People inflicted with spinal cord injury (SCI) are particularly prone to developing pressure ulcers. A pressure ulcer is any lesion caused by unrelieved pressure that results in damage of underlying tissue. Pressure ulcers may develop following a prolonged period of compression of the tissue between a bony prominence and a surface.

Unrelieved pressure may result in occlusion of capillaries and lead to ischemia, which has historically been considered a major factor leading to pressure ulcer formation. The cost of treating an individual pressure ulcer ranges up to $40,000 but can exceed $100,000 depending on severity of the wound. Up to 24% of persons residing in nursing homes reportedly have developed a pressure ulcer (also called bed sores). When a person is in a seated position, his or her weight typically rests on a section of the pelvic girdle called the ischial tuberosity (specifically, the inferior, posterior portion of the ischium). There are two of these bony swellings, left and right, sometimes called the sitting bones, which are located on the posterior, inferior portion of the ischium. The gluteus maximus muscle lies over it when a person is standing; however, when he or she sits down, the muscle shifts to a position that exposes the ischium tuberosity, which then bears the majority of the weight, and pressure ulcers may occur.

Pressure ulcers are a frequently occurring healthcare problem throughout the world. Pressure ulcers pose a significant threat to the quality of life for people confined to wheelchairs, such as persons inflicted with spinal cord injury (SCI). Pressure ulcers once formed may lead to sepsis and early death. Pressure ulcers remain the most common secondary condition associated with SCI, and has been reported to occur in from 28% to 85% of patients with SCI, often within a few days of injury. It is estimated that more than half of the SCI population will develop at least one pressure ulcer in their lifetimes. In Europe, treatment of illness associated with pressure ulcers has been estimated to result in up to 4% of total healthcare expenditure. The United States alone spends about $1.4 billion annually on the treatment of pressure ulcers for people with SCI. It has been estimated that the cost of treating pressure ulcers is 2.5 times the cost of preventing them. Considering the numbers and cost of treatment, pressure ulcers are an important public health problem. There is an urgent and growing need to develop effective modes of prevention and treatment.

Although wheelchair tilt and recline functions are typically used for pressure ulcer prevention, present approaches cannot determine at what angles wheelchair tilt and recline provide effective prevention of pressure ulcers. Clinicians typically recommend uniform guidance to all patients. However, clinical evidence clearly shows that the SCI individuals demonstrate a wide variety of requirements. Consequently, universal guidelines cannot satisfy all the needs. Hence, personalized configuration of wheelchair tilt and recline for each individual is more desirable and beneficial.

It is known that traditional statistical methods can be used to model biomedical problems. However, statistical methods are found less capable of finding patterns, dealing with data that may contain noise, or analyzing non-linear and dependent data. Artificial intelligent techniques on machine learning, on the other hand, have played increasingly important role in bioinformatics for classifying and mining data. Such techniques can capture patterns based on examples (i.e., training data) even though the underlying nature, principles, and/or probability distributions may not be clear. It is, therefore, an object of the present invention to use an artificial intelligent module (artificial neural network in the current implementation) to provide a method and apparatus with which to discover patterns driven by individual human conditions, operational environments, and outcome or use objectives. It is a further objective of the present invention to provide personalized guidance and configuration control for seating support, adjustment, and positioning including wheelchair tilt and recline usage for people confined to wheelchairs and who may be inflicted with SCI.

SUMMARY OF THE INVENTION

Pressure ulcers (PUs) impose a significant threat to the quality of life of wheelchair users. Prolonged unrelieved seating pressure has been identified as a major causative factor of PUs. Wheelchair tilt and recline (TR) functions are two of the most desirable features on a wheelchair for relieving seating pressure. Tilt refers to a change of the seat angle orientation while maintaining the seat-to-back angle and recline refers to a change of the seat-to-back angle. Despite the importance of TR functions, the majority of the wheelchairs do not offer a built-in mechanism to measure TR angles. Wheelchair users tend to adjust TR angles based on their own perceptions. However, research shows that wheelchair users rarely adjust enough tilt or recline angles to relieve seating pressure, which has been recognized as a major causative factor of pressure ulcers. The reasons for the ineffective usage of wheelchair TR functions are in part due to the lack of a convenient way to measure wheelchair TR angles, and in part due to the lack of a practical way to monitor whether wheelchair users follow the clinical guidelines of wheelchair TR usage.

The present invention enables a user to obtain a set of favorable tilt and recline combinations derived from the user's specific profile that can help reduce the risk of pressure ulcers. A profile may include information comprising the user's age, gender, height, weight, body mass index, level of injury, completeness of injury, duration of injury, age at onset of injury (e.g., SCI, stroke, amputation), whether he/she smokes, drinks alcohol, exercises, and/or has pressure ulcer history. An overall picture of the user's favorable tilt and recline settings are presentable, along with choices to adjust seating positions. Users are also presented with the best TR functions that can most effectively reduce risk of pressure ulcers.

The present invention provides a unique way to effectively use wheelchair TR functions, even though most wheelchairs in use today do not offer a built-in mechanism for measuring TR angles. Smart mobile devices (smartphones and tablets) are configurable using the methods of the present invention to accurately measure TR angles. For example, the advanced computational process of the present invention enables users to conveniently measure wheelchair TR angles by simply positioning a smartphone configured in accordance with the present invention in their pockets (e.g., shirt pocket). Further, through the combined use of mobile and cloud computing, the methods of the present invention enable automatic transmission of wheelchair TR usage information to "cloud-based" storage and remote analysis.

Cloud computing is often defined as the practice of using a network of remote servers hosted on the Internet to store, manage, and process data, rather than a local server or a personal computer. Cloud storage involves storing data on multiple virtual servers that are generally hosted by third parties. The term "cloud" as used herein generally refers to cloud computing, cloud storage, and the world Wide Web. Hence, through the use of cloud computing and web-based approaches, healthcare providers and researchers can effectively monitor whether the TR guidelines are properly carried out in wheelchair users' natural settings (e.g., home, office, community, etc.). The present invention works for both power and manual wheelchairs, provided they are equipped with tilt or tilt and recline functions. Hence, functionality of both new and existing wheelchairs can be significantly improved through use of the present invention.

The present invention may be implemented in multiple non-limiting versions, including a local device (e.g., smartphone) version, a mobile-cloud version, and a web-cloud version. In the local version, all the functionality may be implemented locally in a smartphone, or similar mobile device. This embodiment may be preferable for use by individuals with limited data transfer and bandwidth capacity. However, a fully localized embodiment implies that the same artificial intelligent module will have to be implemented multiple times for different mobile operating systems, such as Android, iOS, and Windows. Alternative embodiments may be preferable for users where data transfer and bandwidth capacity is sufficient. The artificial intelligent module and data storage may be extracted from the local version and implemented as a cloud computing model in the Internet cloud. In this embodiment, only one implementation of the intelligent module is needed, and both the artificial intelligent module and the data storage may be accessed from a mobile device or a web-based user interface. The smartphone application as well as the web application are responsible for collecting user's information, requesting guidance on wheelchair tilt and recline usage or other position parameters, displaying results to the users, and using a goniometer implemented on the local device to measure wheelchair tilt and recline angles.

In a broad aspect, the apparatus of the present invention accepts input that may comprise an individual's demographic information, neurological attributes, physical history, operational environment, and outcome or use objectives, then returning guidance and/or control parameters directed to positioning and adjustment of physical supports for the human body.

In another aspect, the present invention may be embodied as a specific purpose mobile device comprising a computational framework, artificial neural network, a goniometer, and minimum functionality necessary for configuration and control of positioning and adjustment directed to seating supports for the human body.

In another aspect, the present invention provides functions and analytical processes capable of finding patterns, dealing with data that may contain noise, or analyzing non-linear and dependent data.

In yet another aspect, the present invention may be embodied as a specific purpose device integrated into a powered seating apparatus, where the device comprises a computational framework, artificial neural network, a goniometer, and minimum functionality necessary for configuration and control of seating support configuration.

In another aspect, the present invention may comprise a computational framework, artificial neural network, and application instruction set operable on mainstream general purpose mobile devices including "smartphones" (e.g. iPhone 5, Samsung Galaxy), tablets computers (e.g., iPad), Google glass, iWatch, etc., collectively "smart devices," running operating systems such as Android, iOS, and MS-Windows, where such devices include at least an accelerometer.

In another aspect, the artificial neural network in the present invention is embodied as an artificial intelligence (AI) module trained with clinical research data directed to optimal positioning and adjustment of physical supports for the human body for a defined purpose or desired outcome.

In another broad aspect, the apparatus of the present invention accepts input comprising an individual's demographic information, neurological attributes, and pressure ulcer history and provides guidance or control parameters directed to: (1) the favorable wheelchair tilt and recline settings; (2) the optimal wheelchair tilt and recline angles that may most effectively reduce pressure ulcer risks; and (3) the measurement of tilt and recline angles by implementing a goniometer.

In another aspect, the present invention may be configured to provide optimal duration and frequency to perform wheelchair tilt and recline functions in response to input comprising an individual's demographic information, neurological attributes, and pressure ulcer history.

In another aspect, the present invention may be configured to measure wheelchair tilt and recline angles (i.e., a goniometer), periodically remind the wheelchair user of performing wheelchair tilt and recline, record wheelchair tilt and recline usage information, including the time when the wheelchair user performs the tilt and recline functions, the angles of the tilt and recline, the duration on which the user maintains the tilt and recline position, and the derived frequency, i.e., how often the wheelchair user repositions himself/herself by means of wheelchair tilt and recline.

In another aspect, the goniometer can work independently of the artificial neural network and intelligent module, and operable on mainstream general purpose mobile devices including "smartphones" (e.g. iPhone 5, Samsung Galaxy), tablets computers (e.g., iPad), Google glass, iWatch, etc., collectively "smart devices," running operating systems such as Android, iOS, and MS-Windows, where such devices include at least an accelerometer.

In another broad aspect, the present invention may be embodied as a specific purpose mobile device comprising a computational framework, artificial neural network, a goniometer, and minimum functionality necessary for configuration and control of wheelchair tilt and recline.

In yet another aspect, the present invention may be embodied as a specific purpose device integrated into a powered wheelchair, where the device comprises a computational framework, artificial neural network, a goniometer, and minimum functionality necessary for configuration and control of wheelchair tilt and recline.

In another aspect, the present invention may comprise a computational framework, artificial neural network, and application instruction set operable on mainstream general purpose mobile devices including "smartphones" (e.g. iPhone 5, Samsung Galaxy), tablets computers (e.g., iPad), Google glass, iWatch, etc., collectively "smart devices," running operating systems such as Android, iOS, and Windows, where such devices include an accelerometer.

In another broad aspect, the present invention combines mobile computing and artificial intelligence techniques, incorporating an artificial intelligence (AI) module in an application instruction set operable on a mobile device.

In another aspect, the AI module may be trained with clinical research data on clinically recommended tilt and recline angles, and other position parameters.

In another aspect, smart device users may input into the user interface of the present invention their demographic, neurological, and pressure ulcer history information, and recommended wheelchair tilt and recline angles will be determined favorable for the individual to reduce risk of pressure ulcers.

In another aspect of the present invention, the user interface of the present invention may be configured to display the recommended wheelchair tilt and recline angles, or other position parameters.

In another aspect of the present invention, recommended wheelchair tilt and recline angle may be output from a mobile embodiment of the present invention to a control function operating in a powered wheelchair or other powered mobility device.

In another aspect of the present invention, recommended wheelchair tilt and recline angle may be transferred wirelessly to a controller operational to adjust configuration orientation of a powered wheelchair or other powered mobility device.

In a yet another broad aspect of the present invention, an artificial intelligent module is provided comprising an artificial neural network (ANN) having a layered network structure, in which processing units (i.e., neurons) are arranged in layers, where the neurons in adjacent layers can communicate with each other by sending and receiving signals through weighted connections.

In another aspect, the input/output behavior of a neuron is defined by its internal activation function, which accumulates the input signals and then calculates the outputs.

In another aspect, a learning process proceeds in iterations by tuning the weights of connections using a training algorithm (e.g., the back-propagation algorithm).

In another aspect, a user registration component is provided, which allows users to create their own profiles to record their demographic information (e.g., gender, weight, height, etc.), neurological information (e.g., level of injury, completeness of injury, etc.), and pressure ulcer history (i.e., whether he/she once developed pressure ulcers).

In another aspect of the present invention, the output includes (1) a range of tilt and recline angles that are favorable for pressure reduction for the user; and (2) the optimal tilt and recline angles that are most effective in reducing the risk of pressure ulcers.

In another aspect, the present invention may be configured to provide optimal frequency and duration to perform wheelchair tilt and recline functions, including guidance such as "perform tilt and recline every 15 minutes (i.e., frequency) and maintain the tilt and recline setting for at least 3 minutes (i.e., duration)."

In another aspect of the present invention, a goniometer is provided, which uses an accelerometer sensor in a smart device (e.g., smartphone or tablet) to measure angles of wheelchair tilt and recline.

In another aspect of the present invention, a goniometer measures current wheelchair tilt and recline angle and contrasts those angles with guidance angles to generate control parameters that cause the tilt and recline angle of a powered wheelchair or other powered mobility device to be rotated to a precise angular position.

In another aspect of the present invention, a goniometer may be configured to periodically remind the wheelchair user of performing wheelchair tilt and recline, and record wheelchair tilt and recline usage information, including the time when the wheelchair user performs the tilt and recline functions, the angles of the tilt and recline, the duration on which the user maintains the tilt and recline position, and the derived frequency, i.e., how often the wheelchair user repositions himself/herself by means of wheelchair tilt and recline.

In another aspect of the present invention, the goniometer utilizes advanced math and physics methods to establish a model of the mobile device, which is able to accurately measure wheelchair TR angles no matter how the user positions the mobile device. As a result, the wheelchair user can place the smartphone into his/her pocket while accurately measuring the tilt and recline angles.

In another aspect of the present invention, a goniometer uses voice alerts to guide the usage of wheelchair tilt and recline. As a result, the wheelchair user can place the smartphone into his/her pocket while measuring the tilt and recline angles.

In another aspect of the present invention, a goniometer can work independently without relying on the artificial neural network and intelligent module.

In another aspect of the present invention, the network structure and weights of the artificial neural network are determined offline by using clinical research data on clinically recommended tilt and recline angles, or other position parameters.

In another aspect of the present invention, the artificial neural network is fully configurable through adjusting the network structure and weights.

In another aspect of the present invention, the artificial neural network operable in the AI module can be replaced by other artificial intelligence techniques, namely, any classification, clustering, and regression techniques.

In another broad aspect, the present invention is operable in a mobile-to-cloud configuration, where the AI module is implemented in a cloud computing platform, and the use of cloud-computing ("the cloud") will enable smart devices running on different operating systems to share the same AI module in the cloud.

In another aspect of the present invention, where the AI module is operable in the cloud, the smart device will be responsible for at least collecting user's information, requesting guidance on wheelchair tilt and recline usage or other position parameters, displaying results to the users, and using an implemented goniometer to measure wheelchair tilt and recline angles, balancing workload between mobile and cloud and simplifying maintenance and upgrade.

In another aspect of the present invention, where the AI module is operable in the cloud, the smart device may output adjustment parameters to a control device operational in a powered seating apparatus (e.g. powered wheelchair).

In another broad aspect, the present invention provides actionable aural guidance to achieve recommended tilt and recline settings suitable to a particular wheelchair user based on his/her own profile.

In another aspect, the present invention enables measurement, display, and auditory notification of tilt and recline angles in near real-time as a user adjusts tilt and recline settings on a wheelchair.

In another aspect, the present invention provides remote monitoring and analytics as to whether or not wheelchair users follow recommended tilt and recline guidance.

In another broad aspect of the present invention, a goniometer measures current user positioning angles and contrasts those angles with clinical guidance to generate control parameters that cause the seating position of a powered seating apparatus to be altered to a precise angular position.

In another broad aspect of the present invention, a method is provided for determining spatial orientation of a computational device configured with an accelerometer, comprising: providing a positioning model of said computational device, said positioning model including a vector $v=(\alpha_x, \alpha_y, \alpha_z)$ representing accelerations in three axes measured by said accelerometer; utilizing the dot product property $\theta = \arccos(v_1 \cdot v_2/|v_1| \times |v_2|)$ to calculate angle changes between at least two vectors; where dynamic positioning of said computational device is calculated relative to any reference physical orientation.

In another aspect, the present invention includes the computational device implemented on a mobile device configured to measure incline angles which may include tilt and recline angles.

BRIEF DESCRIPTION OF THE DRAWINGS

FIG. 6 is a non-limiting diagram showing top-level code structure for web-cloud configuration.

DETAILED DESCRIPTION OF PREFERRED EMBODIMENTS OF THE INVENTION

Figure 1:
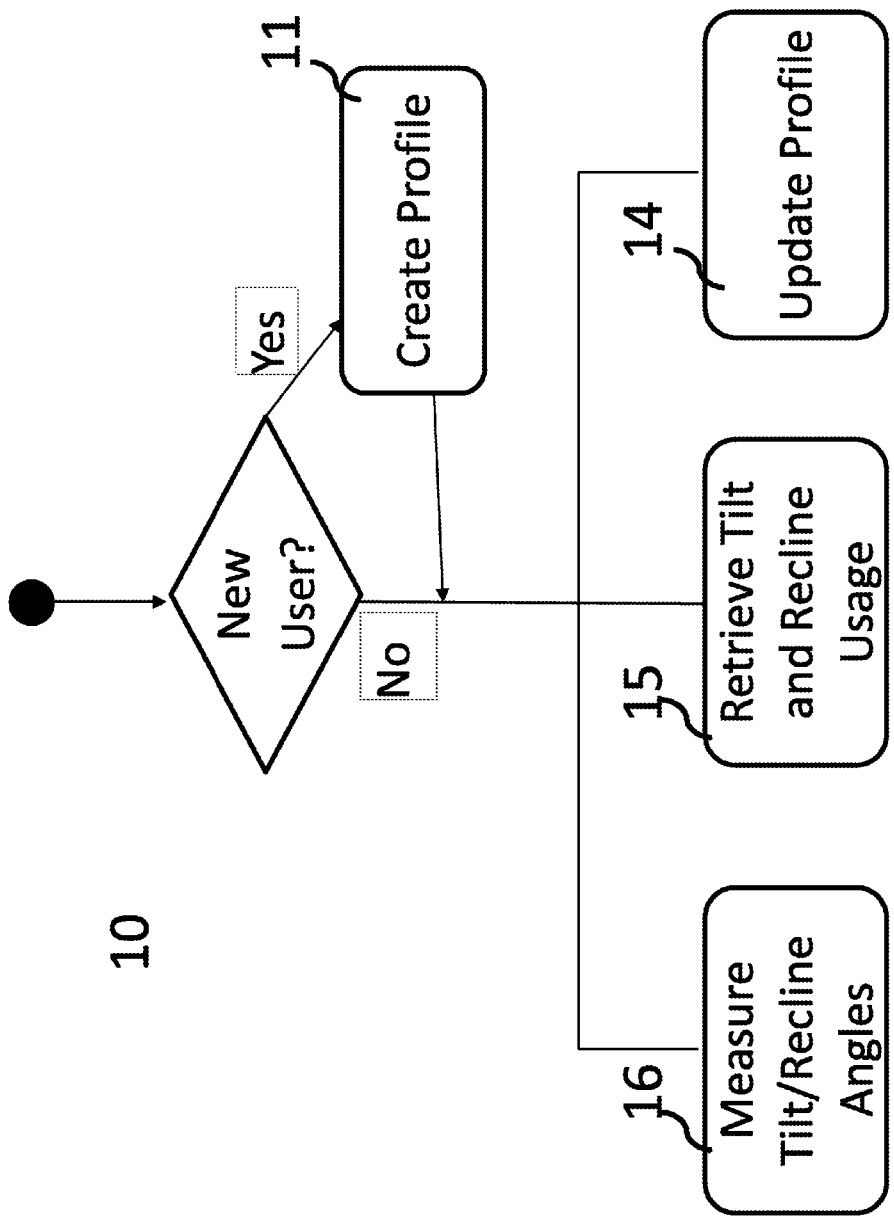
FIG. 1 is a non-limiting diagram showing a process flow directed to an embodiment of the present invention using a smartphone implementation (i.e., the local version). Users must create their profiles before they can use the system. A profile may include information comprising the user's age, gender, height, weight, body mass index, level of injury, completeness of injury, duration of injury, age at onset of SCI, whether he/she smokes, drinks alcohol, exercises, and/or has pressure ulcer history.

In brief: FIG. 1 is a non-limiting diagram showing the process flow directed to use of a smartphone implementation of the present invention (i.e., the local version). Users must create their profiles before they can use the system. A profile may include information comprising the user's age, gender, height, weight, body mass index, level of injury, completeness of injury, duration of injury, age at onset of SCI, whether he/she smokes, drinks alcohol, exercises, and/or has pressure ulcer history. With a valid profile, the user has the options to update his/her profile, retrieve recommendations for wheelchair tilt & recline usage, and use the goniometer implemented in the smartphone to measure wheelchair tilt/recline angles.

Figure 2:
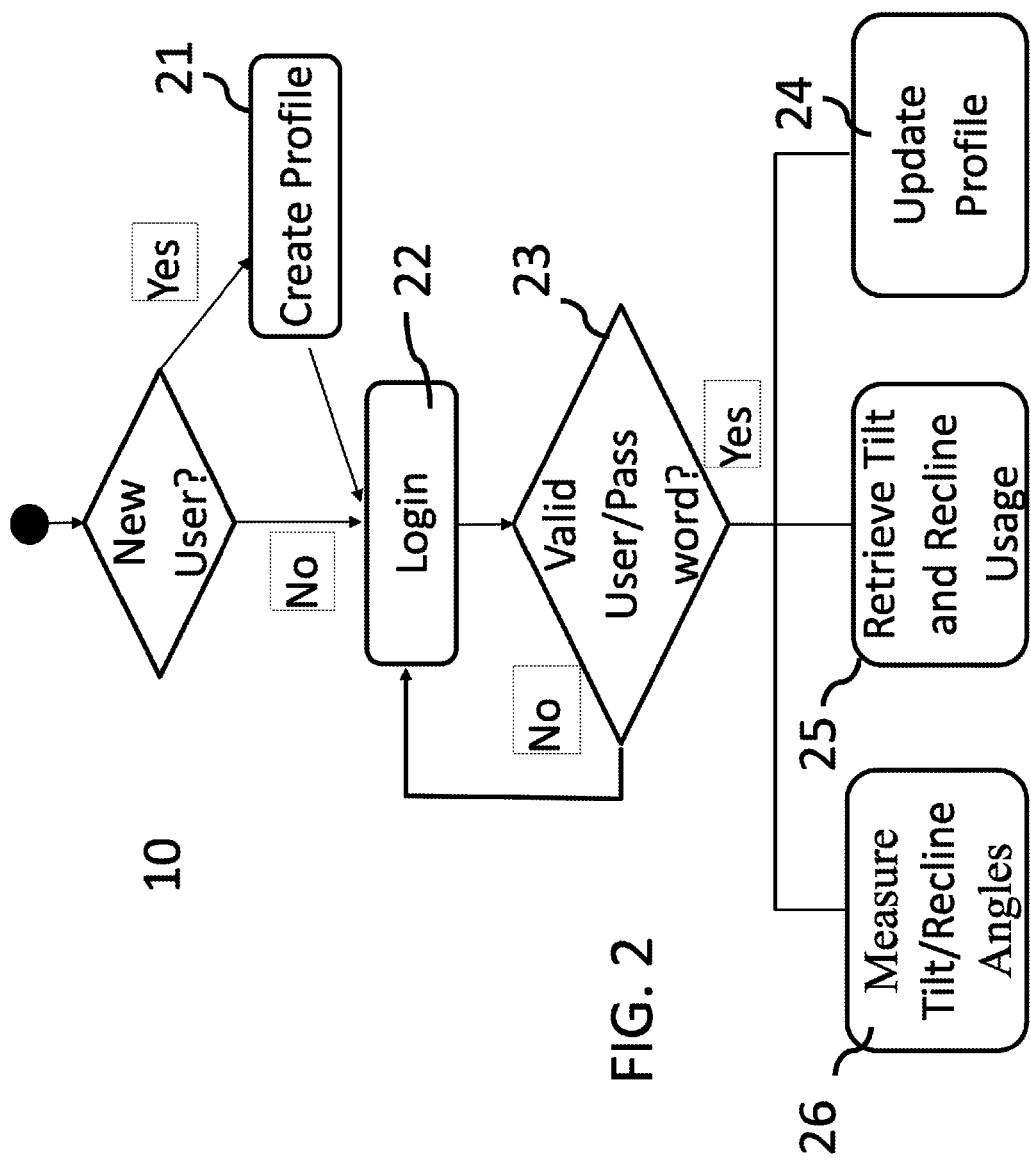
FIG. 2 is a non-limiting diagram showing a process flow directed to an embodiment of the present invention using the mobile-to-cloud implementation. Users must register to create their profiles before they can login. A profile may include information comprising the user's age, gender, height, weight, body mass index, level of injury, completeness of injury, duration of injury, age at onset of SCI, whether he/she smokes, drinks alcohol, exercises, and/or has pressure ulcer history.

FIG. 2 is a non-limiting diagram showing the process flow directed to use of the mobile-to-cloud implementation of the present invention. Users must register to create their profiles before they can login. A profile may include information comprising the user's age, gender, height, weight, body mass index, level of injury, completeness of injury, duration of injury, age at onset of SCI, whether he/she smokes, drinks alcohol, exercises, and/or has pressure ulcer history. In addition, the user needs to choose a user name and password. If a user can provide a valid user name and password, he/she can proceed to use the implemented smartphone application. The user has the options to update his/her profile, retrieve recommendations for wheelchair tilt & recline usage, and use the goniometer implemented in the smartphone to measure wheelchair tilt/recline angles.

Figure 3:
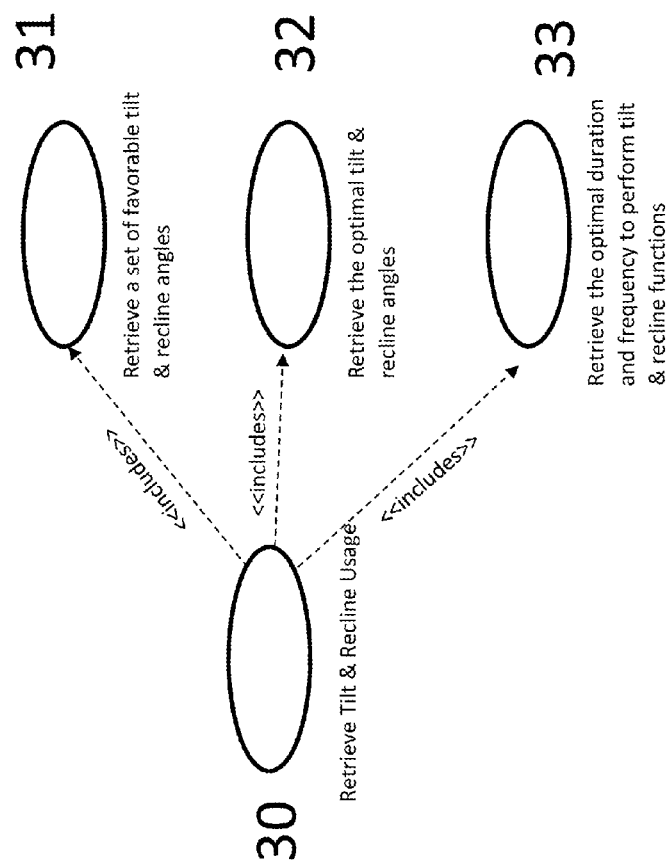
FIG. 3 is a non-limiting diagram presenting the function of "retrieve wheelchair tilt & recline usage". Specifically, users can obtain a set of favorable incline angles including tilt and recline combinations that can help reduce the risk of pressure ulcers.

FIG. 3 is a non-limiting diagram presenting the function of "retrieve wheelchair tilt & recline usage." Specifically, users can obtain a set of favorable incline angles including tilt and recline combinations that can help reduce the risk of pressure ulcers. An overall picture of a user's favorable tilt and recline settings are presentable, along with choices to adjust seating positions. Users are also presented with the best tilt and recline settings that can most effectively reduce risk of pressure ulcers. Users may select the option "retrieve optimal wheelchair tilt and recline setting". The option of retrieving the optimal duration and frequency to perform wheelchair tilt and recline may be selected. Users may retrieve information directed to how often (i.e., frequency) they should perform wheelchair tilt and recline functions and how long (i.e., duration) each time they should maintain at that tilt and recline setting.

Figure 4:
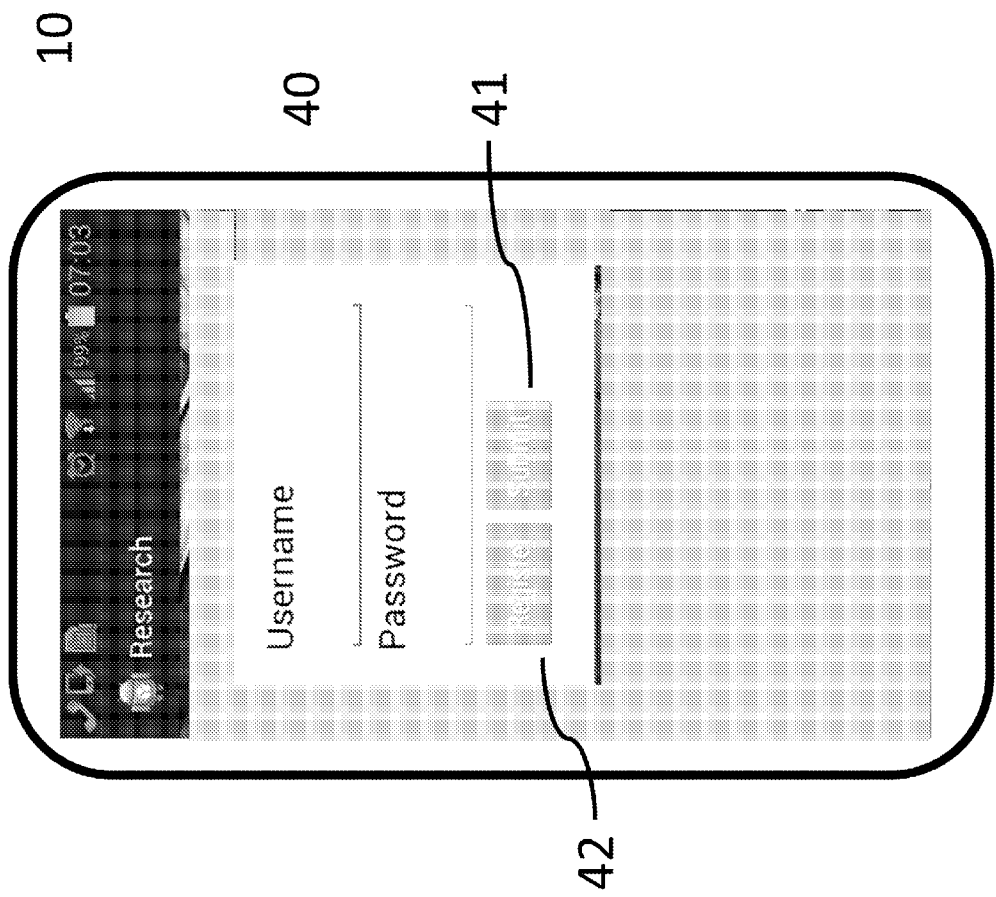
FIG. 4a is a non-limiting diagram showing a screen shot of a smartphone implementation.
FIG. 4b is a non-limiting diagram showing a screen shot of a web-based implementation.
FIG. 4c is a non-limiting diagram showing the structure of a sample artificial neural network.
Figure 4:
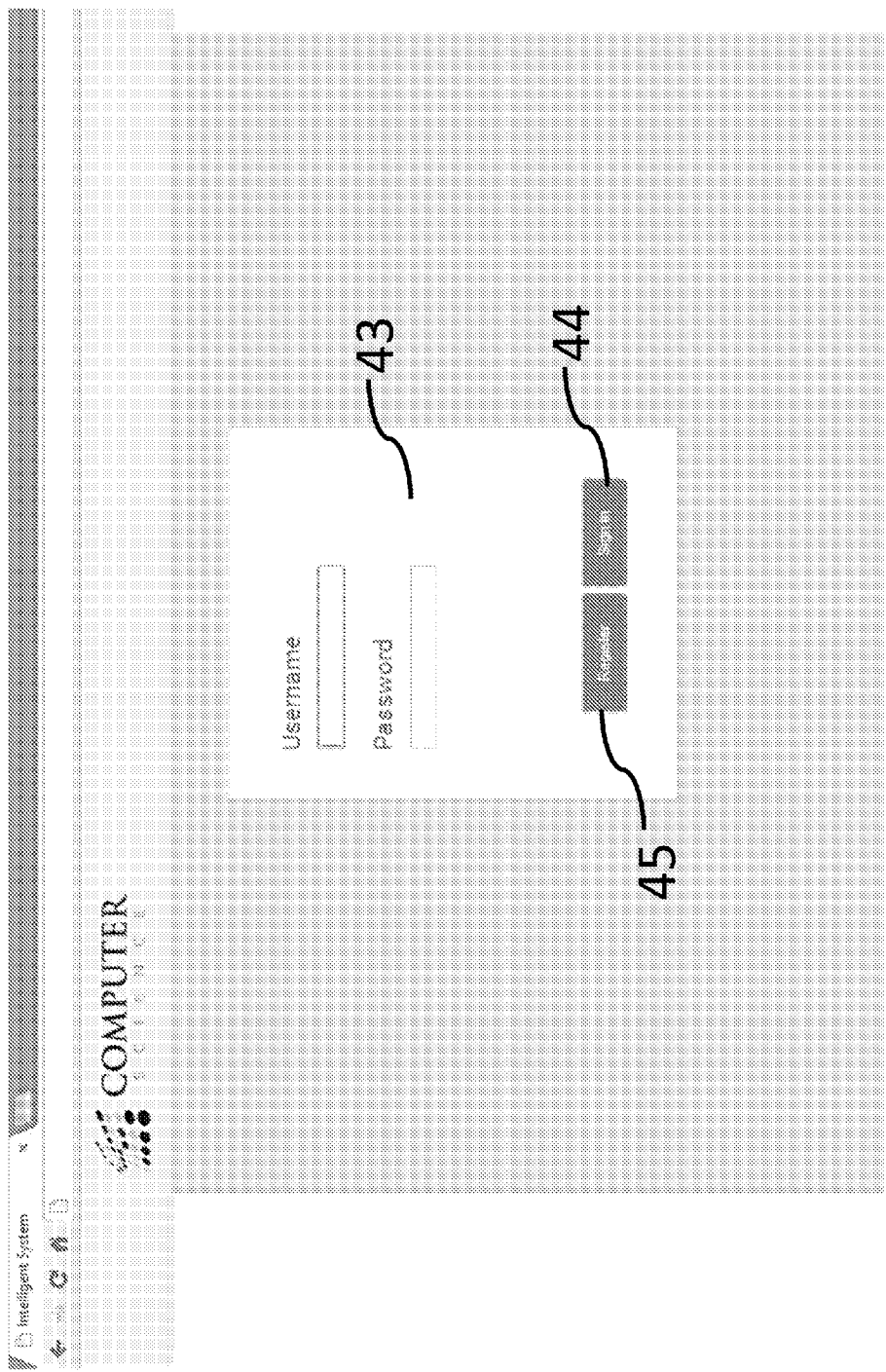
Figure 4:
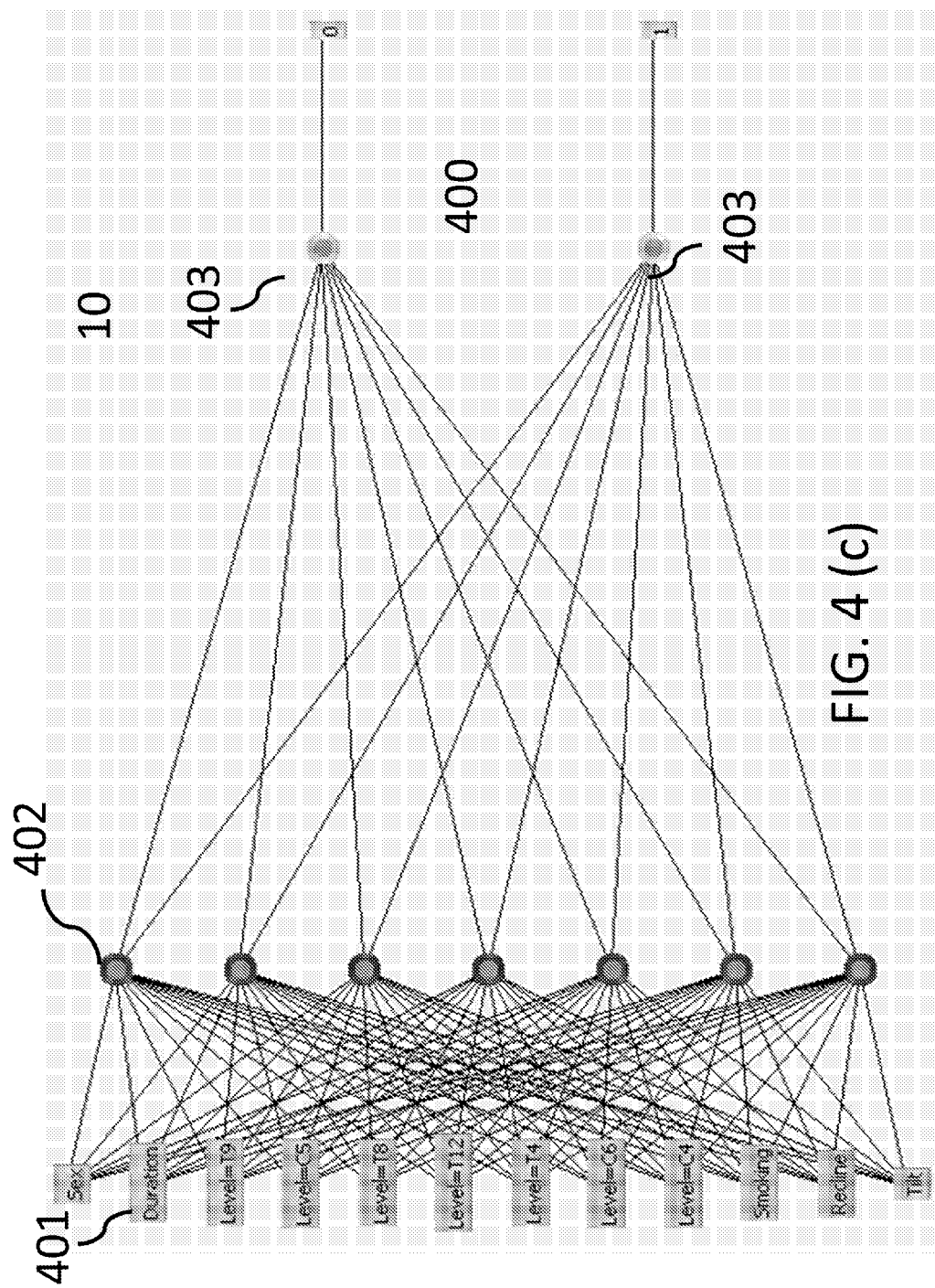

FIG. 4a is a non-limiting diagram showing a screen shot of a smartphone implementation for the mobile-to-cloud version. A user can choose "submit" if he/she is an existing user. Otherwise, the user needs to register first.

FIG. 4b is a non-limiting diagram showing a screen shot of a web-based implementation. A user can choose "submit" if he/she is an existing user. Otherwise, the user needs to register first.

FIG. 4c is a non-limiting diagram showing the structure of an artificial neural network. It consists of three layers, which are input layer, hidden layer, and output layer arranged from left to right.

Figure 5:
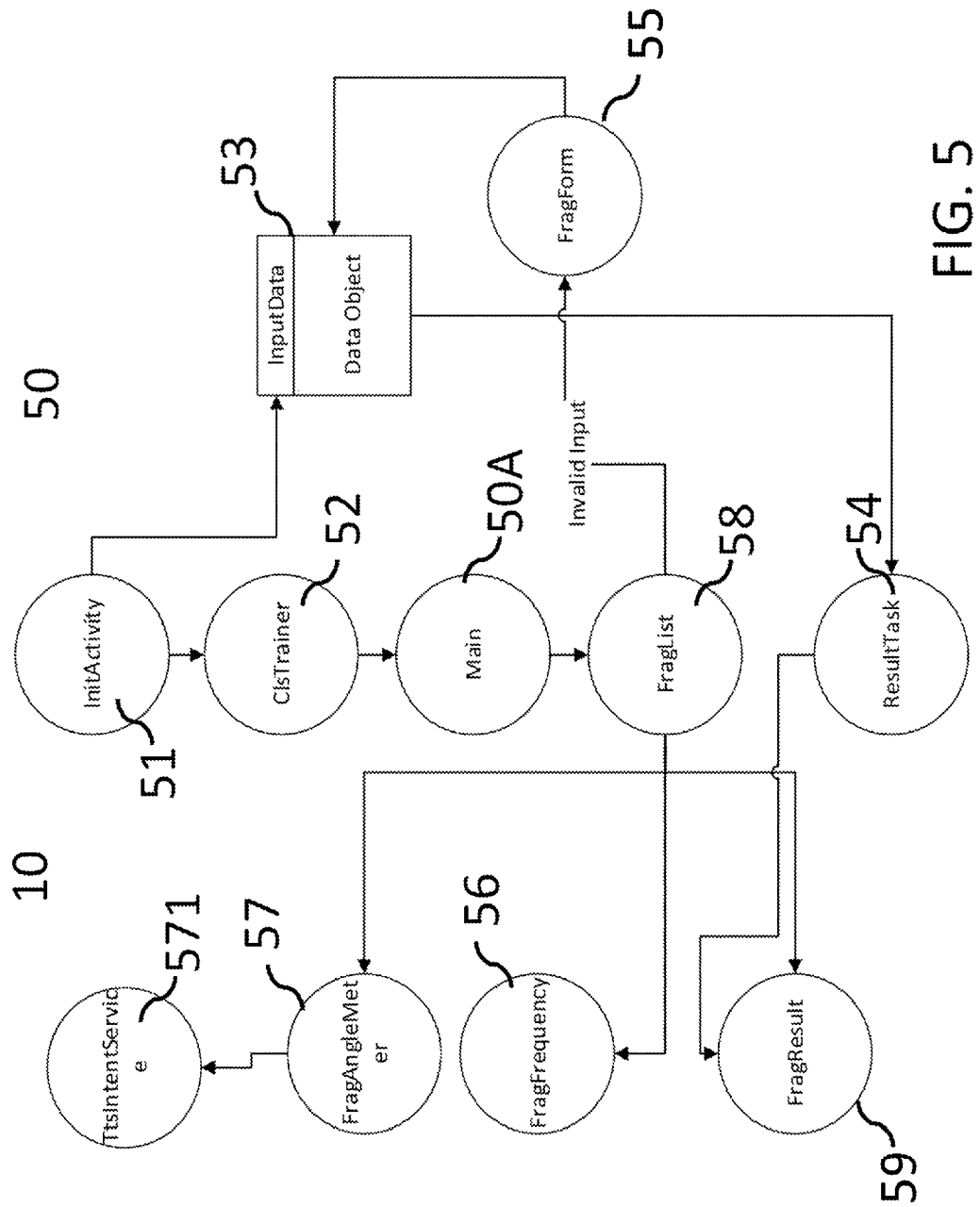
FIG. 5 is a non-limiting diagram showing top-level code structure for a smart mobile device application (i.e., the local version).

FIG. 5 is a non-limiting diagram showing top-level code structure for a smart device application (i.e., the local version). The code structure comprises the following modules: InitActivity, ClsTrainer, Main, InputData, ResultTask, FragmentForm, FragmentFrequency, FragmentAngleMeter, FragmentList, and FragmentResult.

Figure 6:
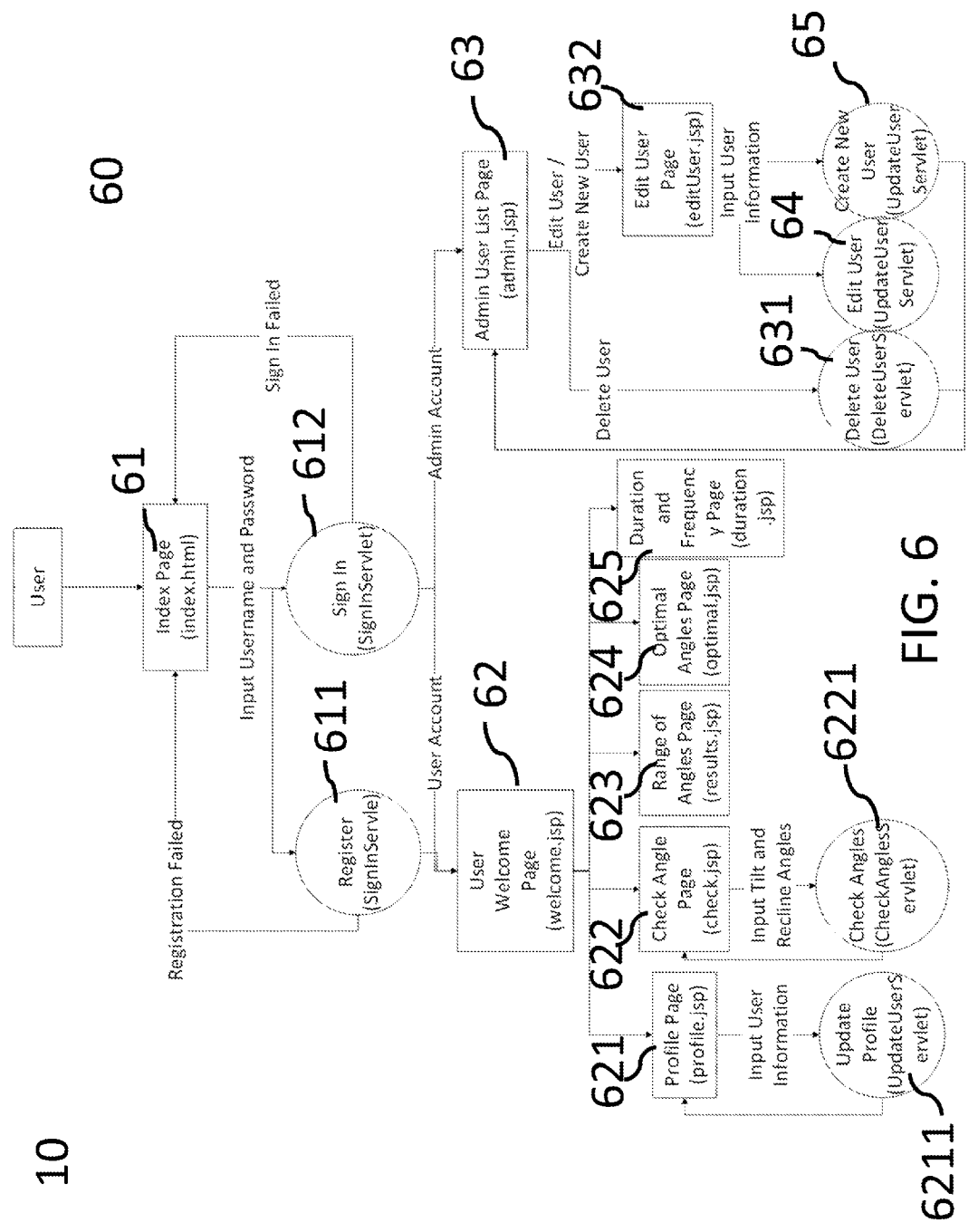

FIG. 6 is a non-limiting diagram showing top-level data flow for a web-based configuration. The code structure for the web-based configuration comprises the following modules: Index Page (index.html), Register (SignInServlet), Sign in (SignInServlet), User Welcome Page (welcome.jsp), Profile Page (profile.jsp), Update Profile (UpdateUserServlet), Check Angle Page (check.jsp), Check Angles (CheckAnglesServlet), Range of Angles Page (result.jsp), Optimal Angle Page (optimal.jsp), Duration and Frequency Page (duration.jsp), Admin User List Page (admin.jsp), Delete User (DeleteUserServlet), Edit User Page (edituser.jsp), Edit User (UpdateUserServlet), and Create New User (UpdateUserServlet).

Figure 7:
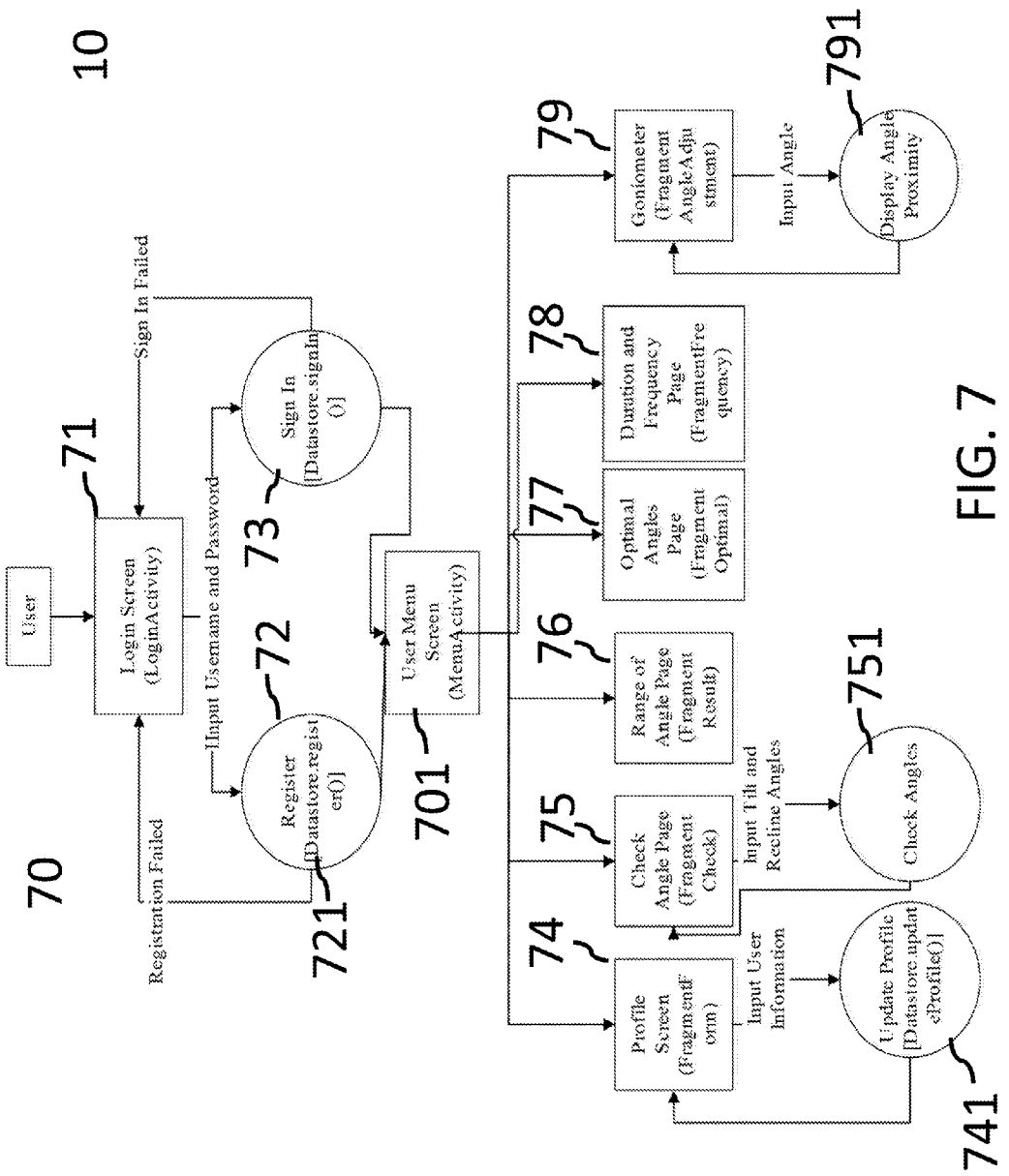
FIG. 7 is a non-limiting diagram showing top-level code structure for mobile-to-cloud configuration using the Android operating system.

FIG. 7 is a non-limiting diagram showing top-level code structure for mobile-to-cloud configuration using the Android operating system. The code structure includes Register, Sign In, Main Menu Screen (MenuActivity), Profile Screen (FragmentForm), Check Angle Page (FragmentCheck), Range of Angles Page (FragmentResult), Optimal Angles Page (FragmentOptimal), Duration and Frequency Page (FragmentFrequency), and Goniometer (FragmentAngleAdjustment).

Figure 8:
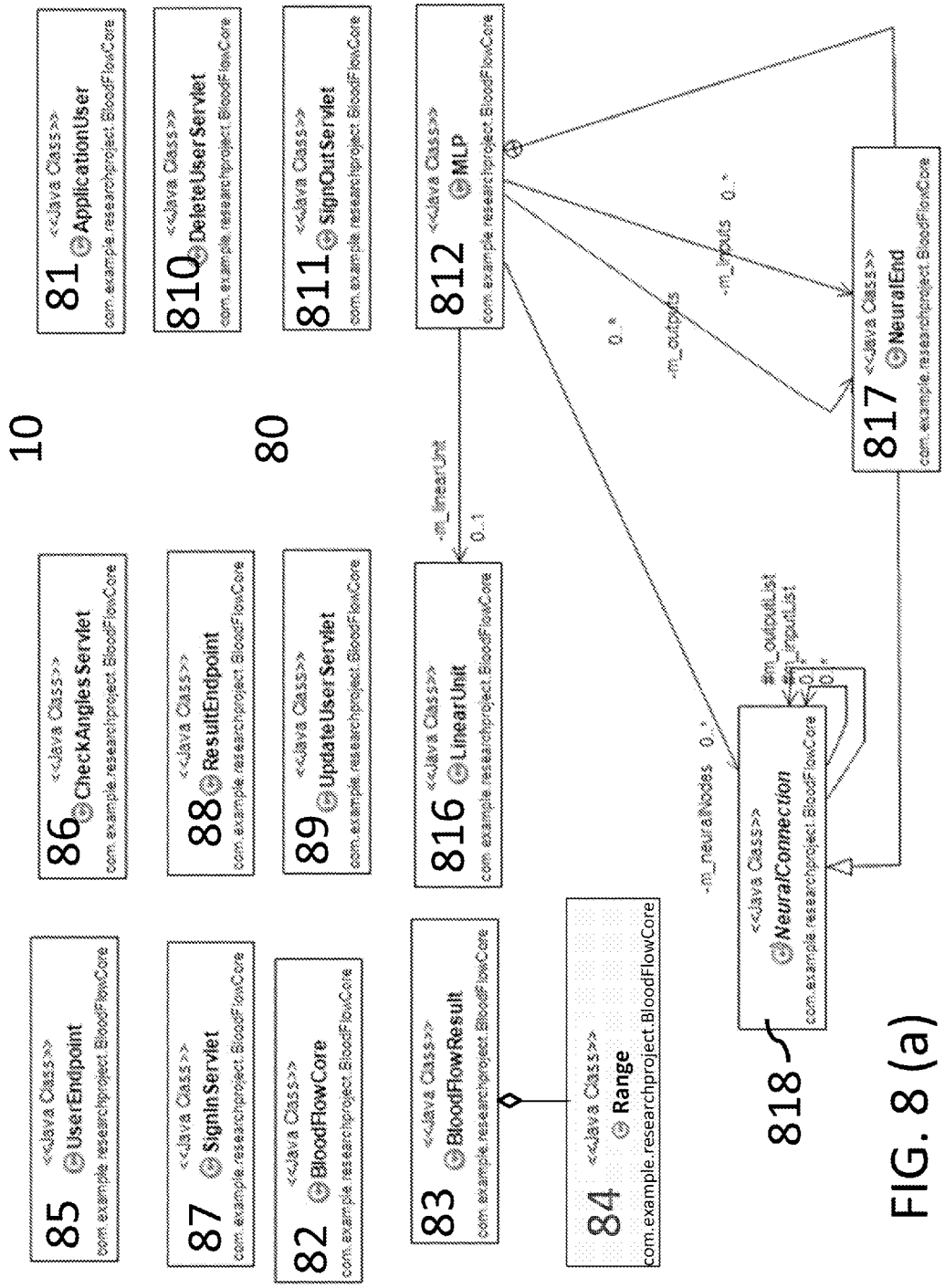
FIG. 8(a) is a non-limiting diagram showing a class diagram for the Google App Engine (GAE, i.e., cloud) configuration where the classes are used to compute personalized guidance on wheelchair tilt and recline usage, and interact with the mobile and web applications.
FIG. 8(b) is a non-limiting diagram showing a class diagram for Google App Engine (cloud) configuration of the present invention where the classes are used to store the tilt and recline usage information (the time when the user performs the tilt and recline functions, the angles of the tilt and recline, etc.)

FIG. 8(a) is a non-limiting diagram showing a class diagram for a GAE (cloud) configuration where the classes are used to compute personalized guidance on wheelchair tilt and recline usage, and interact with the mobile and web applications. The code structure includes: ApplicationUser, BloodFlowCore, BloodFlowResult, Range, UserEndpoint, CheckAnglesServlet, SignInServlet, ResultEndpoint, UpdateUserServlet, DeleteUserServlet, SignOutServlet, MLP, LinearUnit, NeuralEnd, and NeuralConnection.

Figure 8B:
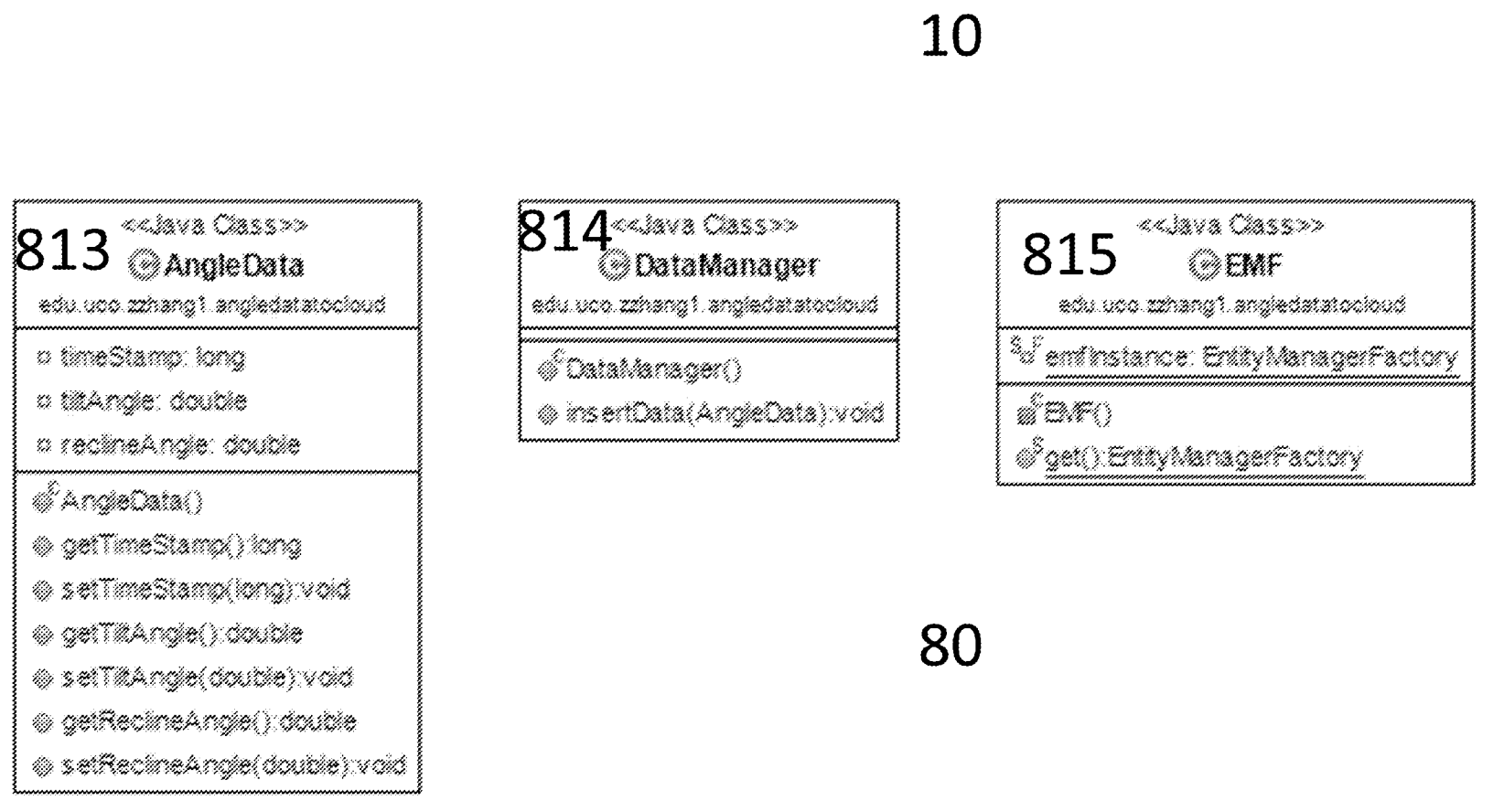

FIG. 8(b) is a non-limiting diagram showing a class diagram for the GAE (cloud) configuration of the present invention where the classes are used to store the tilt and recline usage information (the time when the user performs the tilt and recline functions, the angles of the tilt and recline, etc.) The code structure includes: AngleData, DataManager, and EMF.

Figure 9:
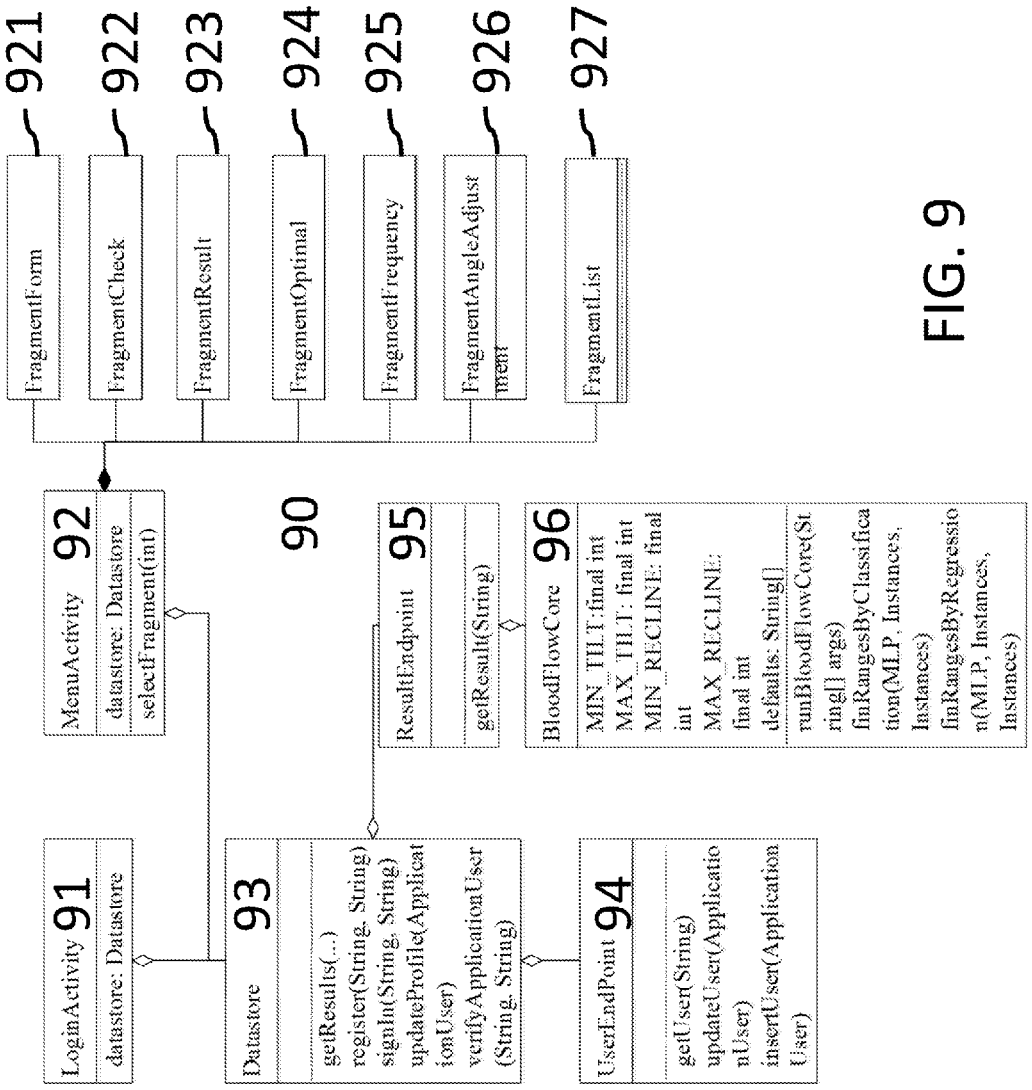
FIG. 9 is a non-limiting diagram showing a class diagram for a mobile configuration using the Android operating system (complementing FIG. 7).

FIG. 9 is a non-limiting diagram showing a class diagram for a mobile configuration using the Android operating system (complementing FIG. 7). The code structure includes: LoginActivity, MenuActivity, FragmentForm, FragmentCheck, FragmentResult, FragmentOptimal, FragmentFrequency, FragmentAngleAdjustment, FragmentAngleMeter, Datastore, UserEndpoint, ResultEndpoint, BloodFlowCore, LoginActivity, MenuActivity, FragmentForm, FragmentCheck, FragmentResult, FragmentOptimal, FragmentFrequency, Datastore, UserEndpoint, ResultEndpoint, and BloodFlowCore.

Figure 10:
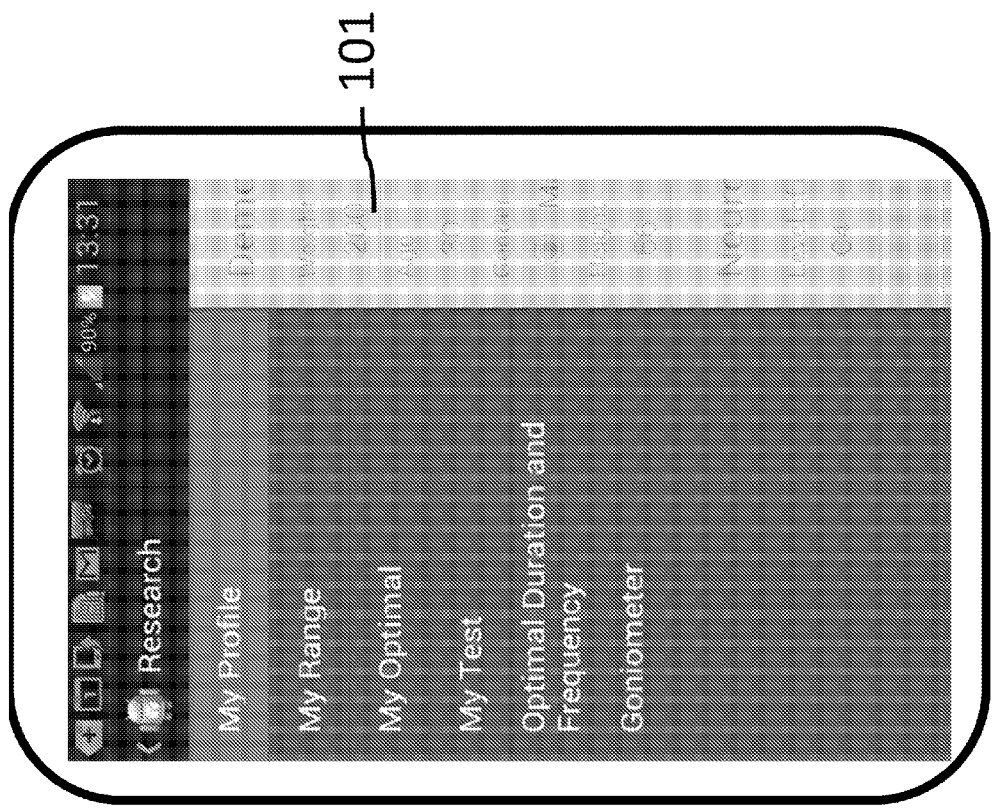
FIG. 10a is a non-limiting diagram showing a screen shot of a smartphone implementation providing a user interface to access system functions.
FIG. 10b is a non-limiting diagram showing a screen shot of a web-based implementation providing a user interface to access system functions.
Figure 10:
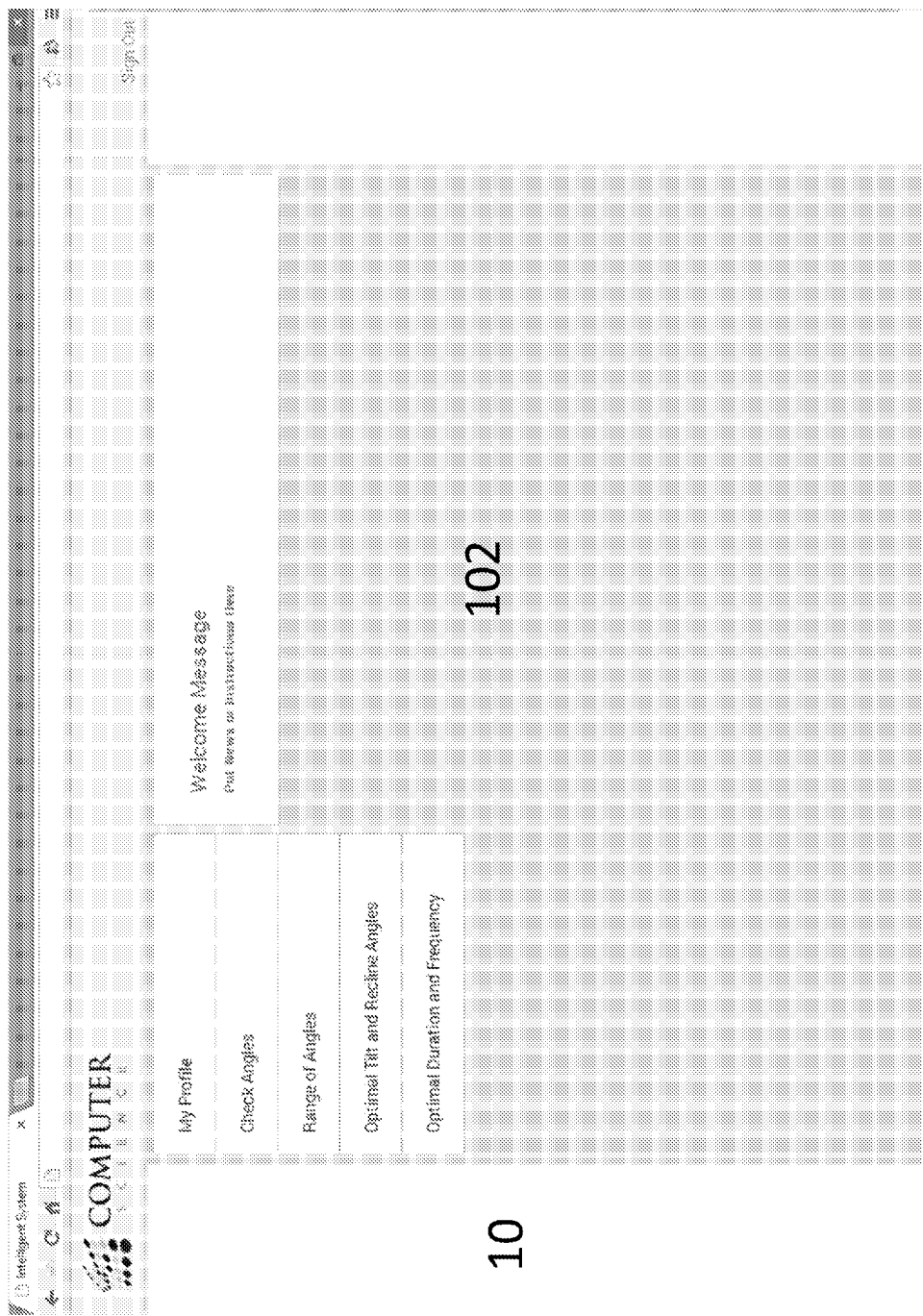

FIG. 10a is a non-limiting diagram showing a screen shot of a smartphone implementation providing a user interface to access system functions. System responses are anticipated to at least user touch and voice commands. Audio recitation and response for visually impaired individuals is anticipated.

FIG. 10b is a non-limiting diagram showing a screen shot of a web-based implementation providing a user interface to access system functions. System responses are anticipated to at least user touch and voice commands. Audio recitation and response for visually impaired individuals is anticipated.

Figure 11:
FIG. 11a is a non-limiting diagram showing a screen shot of a smartphone implementation providing a user interface to enter demographic attributes.
FIG. 11b is a non-limiting diagram showing a screen shot of a web-based implementation providing a user interface to enter demographic attributes.
Figure 11:
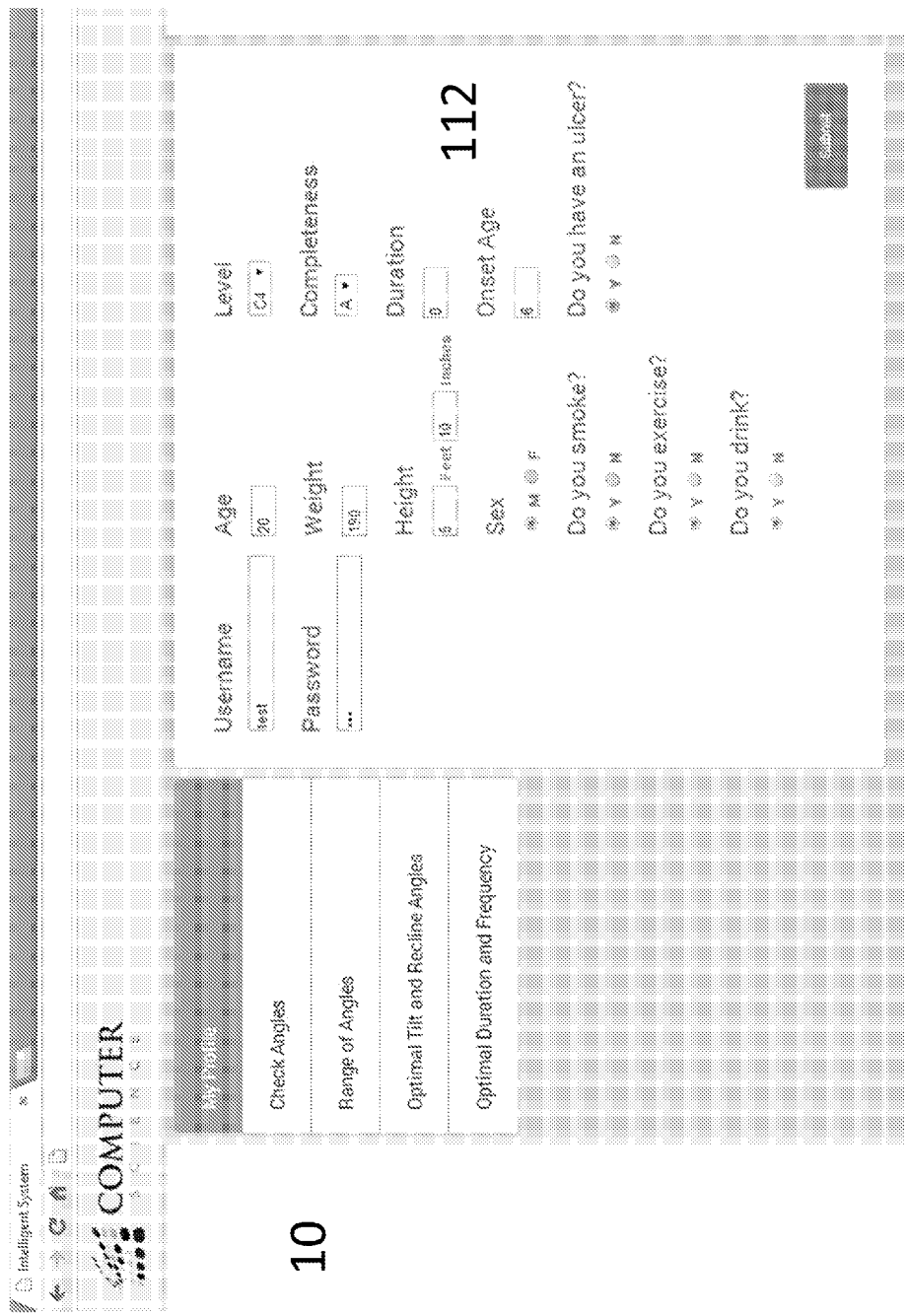

FIG. 11a is a non-limiting diagram showing a screen shot of a smartphone implementation providing a user interface to enter demographic attributes. System responses are anticipated to at least user touch and voice commands. Audio recitation and response for visually impaired individuals is anticipated.

FIG. 11b is a non-limiting diagram showing a screen shot of a web-based implementation providing a user interface to enter demographic attributes. System responses are anticipated to at least user touch and voice commands. Audio recitation and response for visually impaired individuals is anticipated.

Figure 12:
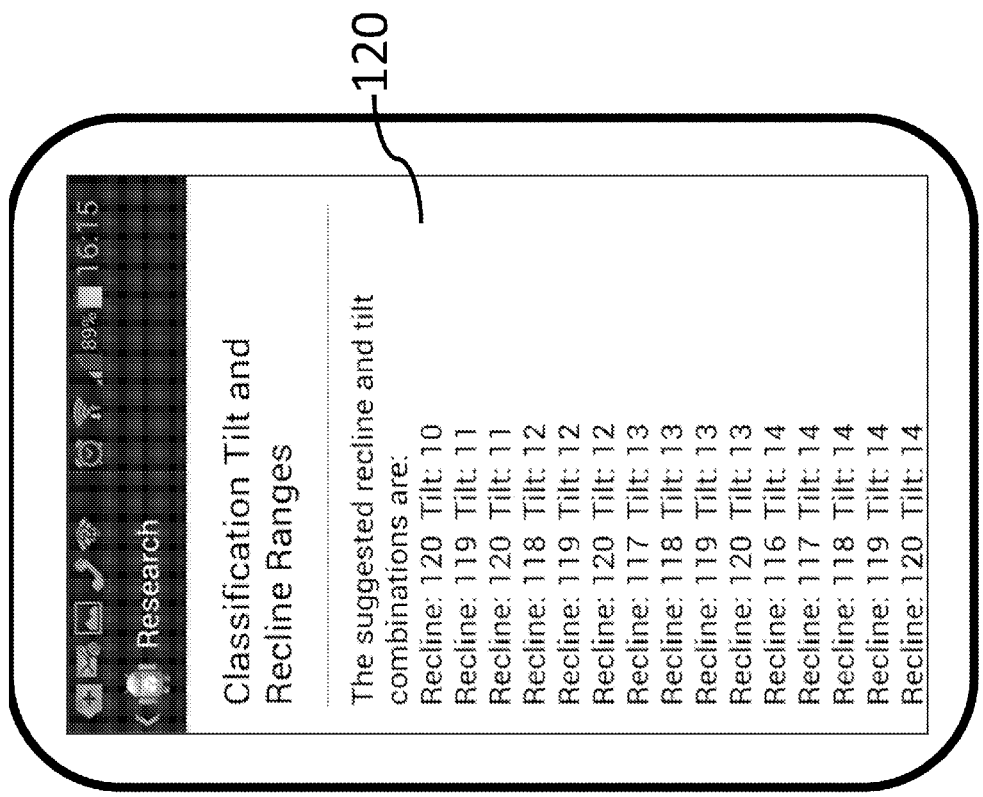
FIG. 12a is a non-limiting diagram showing a screen shot of a smartphone implementation providing a user interface to display favorable tilt and recline angles.
FIG. 12b is a non-limiting diagram showing a screen shot of a web-based implementation providing a user interface to display favorable tilt and recline angles.
FIG. 12c is a non-limiting diagram showing a screen shot of a smartphone implementation providing a user interface to display the best tilt and recline angles for the user.
FIG. 12d is a non-limiting diagram showing a screen shot of a web-based implementation of the present invention providing a user interface to display the best tilt and recline angle for the user.
Figure 12:
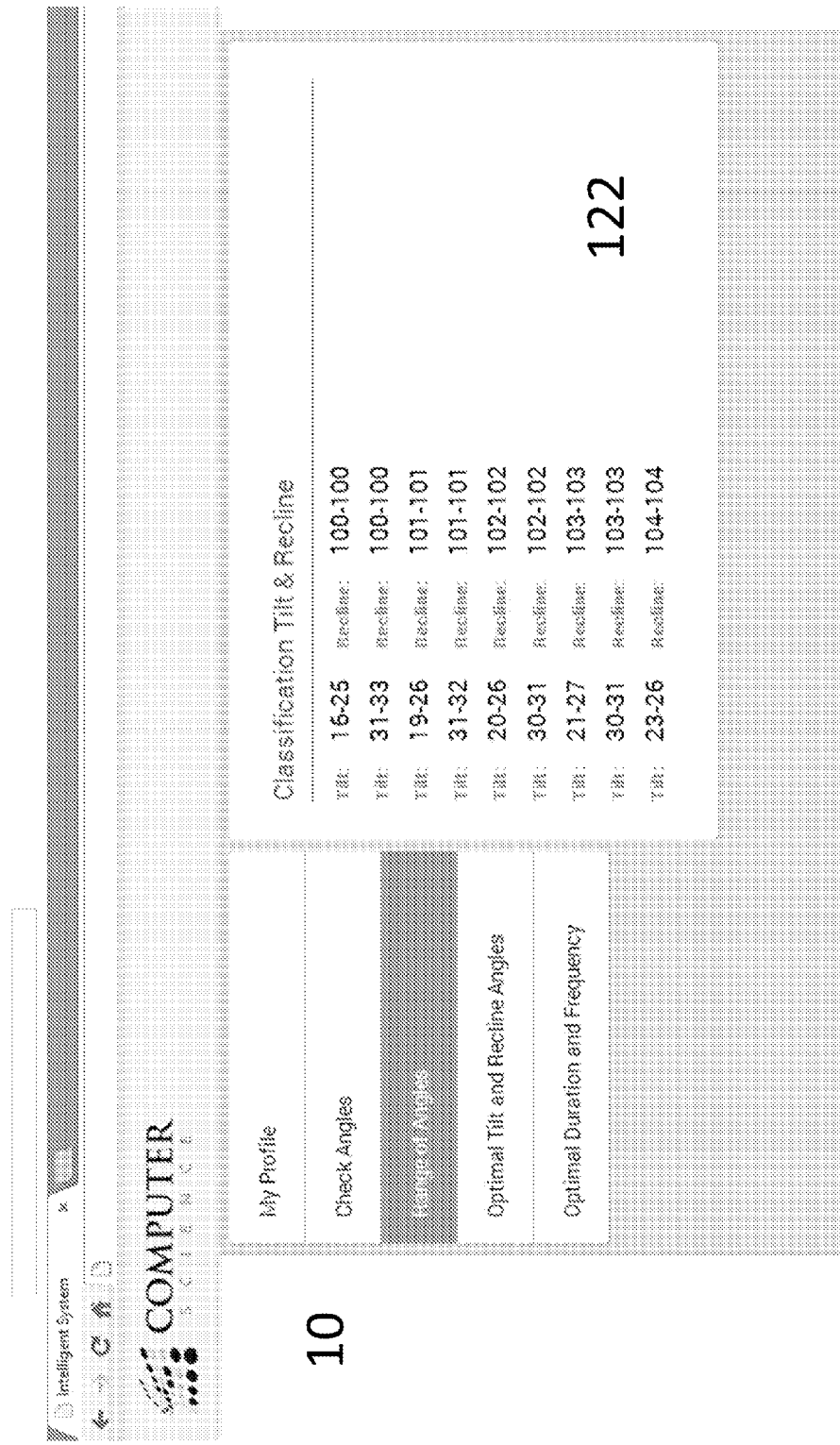
Figure 12:
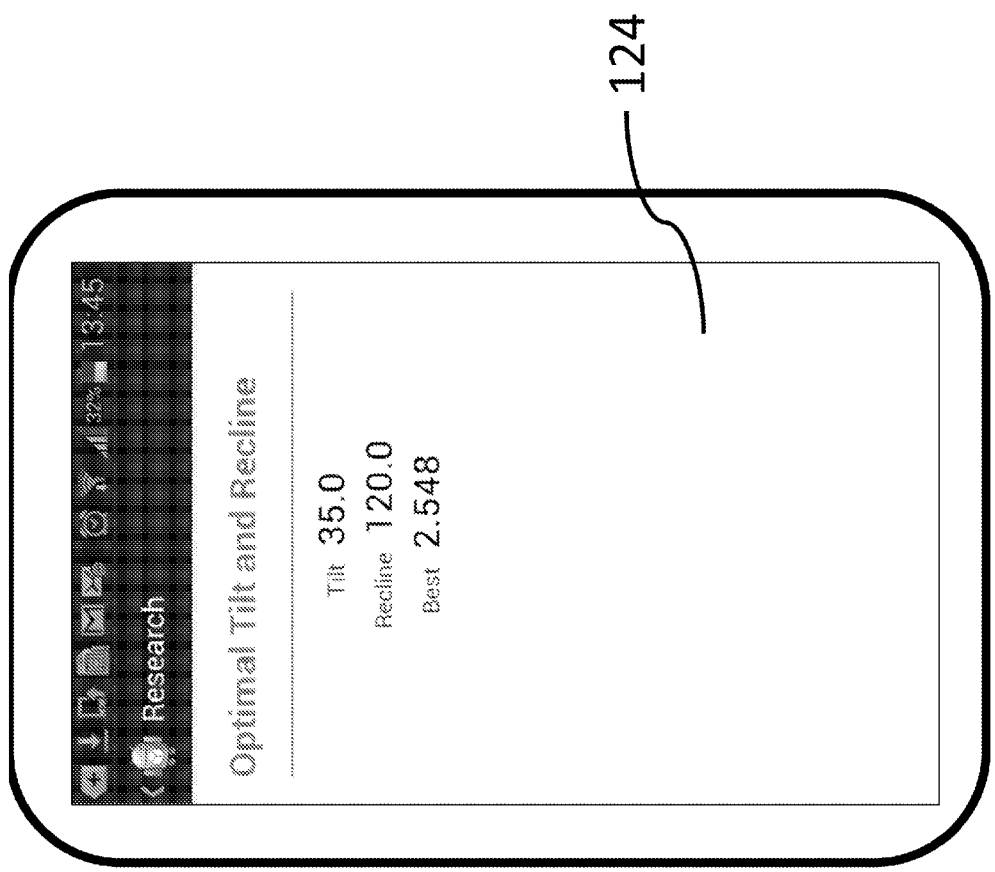
Figure 12:
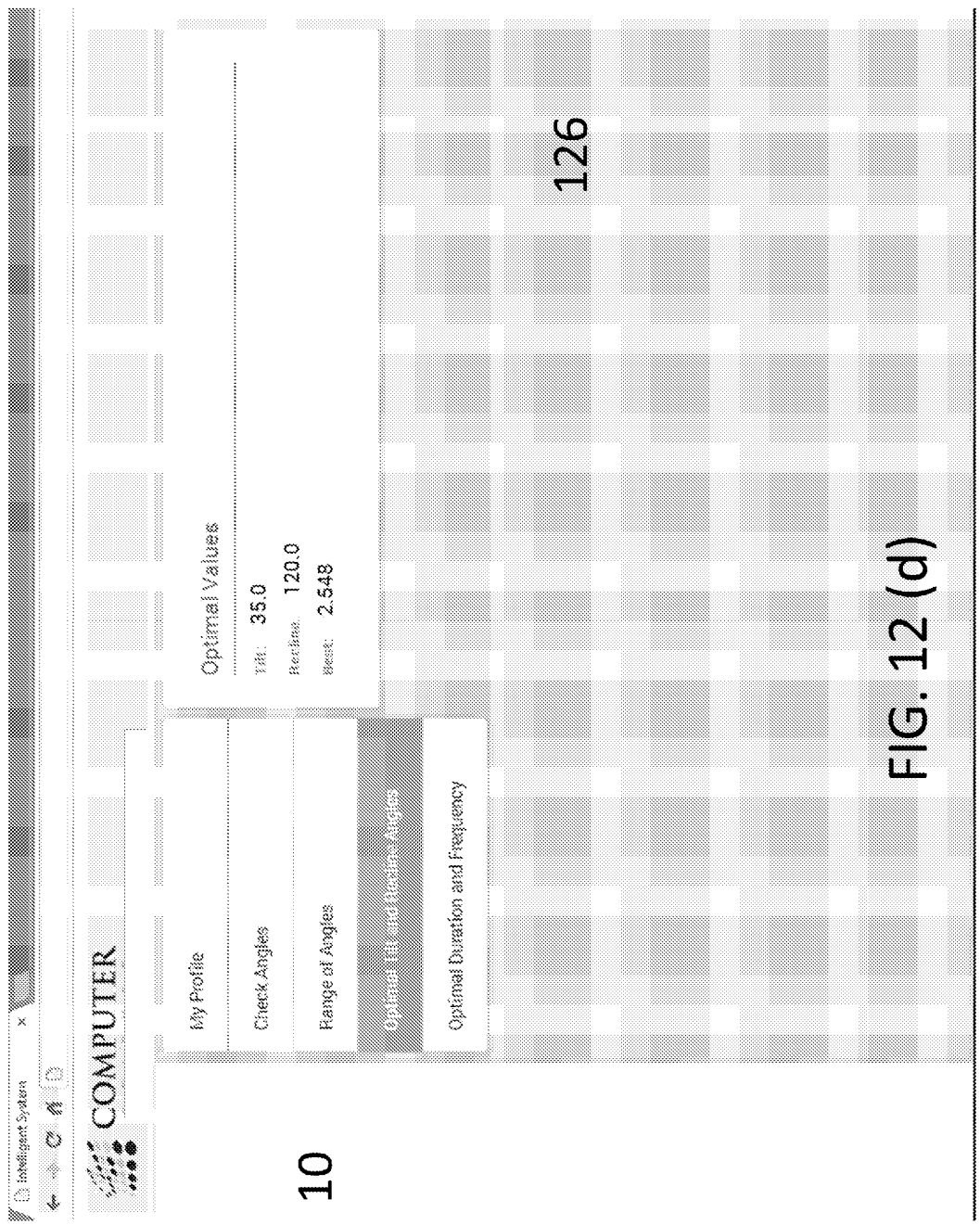

FIG. 12a is a non-limiting diagram showing a screen shot of a smartphone implementation providing a user interface to display favorable tilt and recline angles. System responses are anticipated to at least user touch and voice commands. Audio recitation and response for visually impaired individuals is anticipated.

FIG. 12b is a non-limiting diagram showing a screen shot of a web-based implementation providing a user interface to display favorable tilt and recline angles. System responses are anticipated to at least user touch and voice commands. Audio recitation and response for visually impaired individuals is anticipated.

FIG. 12c is a non-limiting diagram showing a screen shot of a smartphone implementation providing a user interface to display the best tilt and recline angle for a user. System responses are anticipated to at least user touch and voice commands. Audio recitation and response for visually impaired individuals is anticipated.

FIG. 12d is a non-limiting diagram showing a screen shot of a web-based implementation providing a user interface to display the best tilt and recline angle for a user. System responses are anticipated to at least user touch and voice commands. Audio recitation and response for visually impaired individuals is anticipated.

Figure 13:
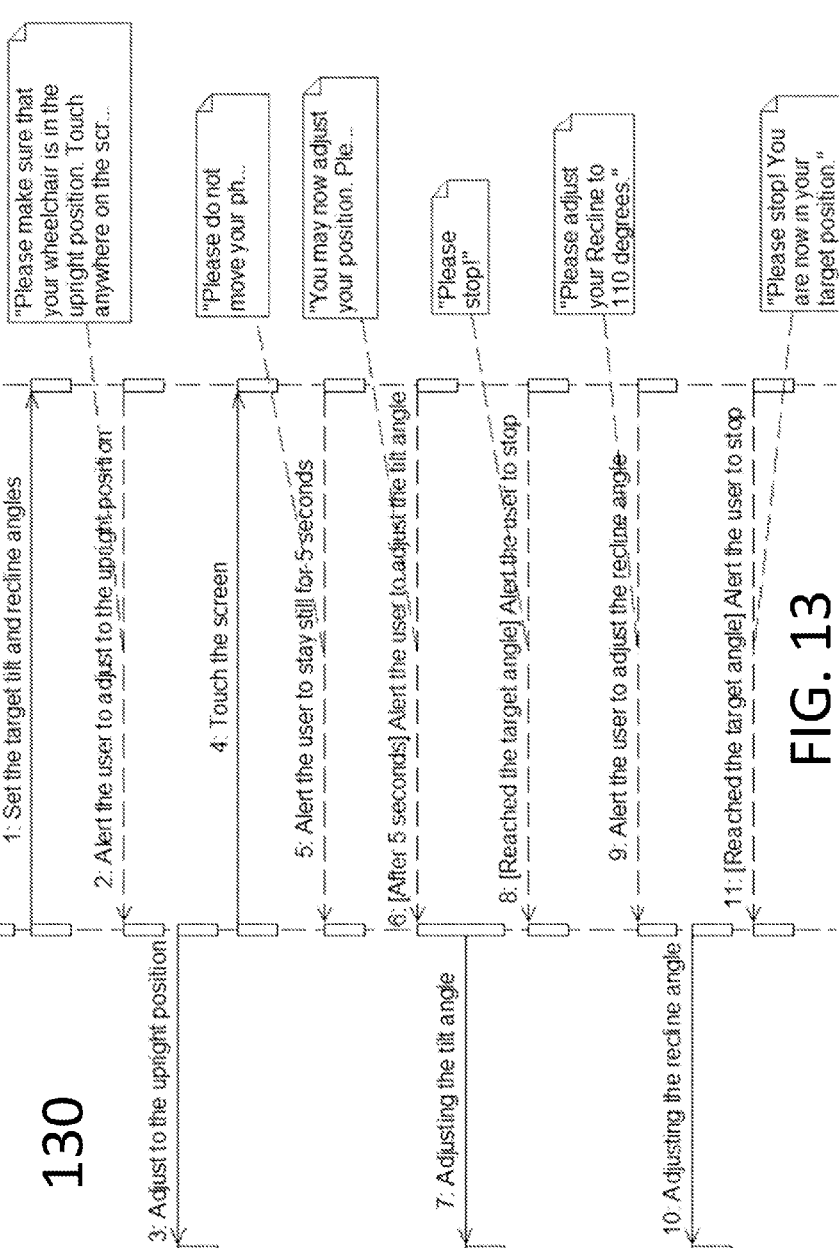
FIG. 13 is a non-limiting sequence diagram showing the process for determining proper adjustment of tilt and recline settings as determined by the present invention, and aided by actionable aural guidance provided by the present invention.

FIG. 13 is a non-limiting diagram showing the process for determining proper adjustment of tilt and recline settings as determined by the present invention. Measurement, display, and auditory notification of tilt and recline angles are accomplished in substantially real-time as a user adjusts tilt and recline settings on a wheelchair. Actionable aural guidance is provided to enable the user to achieve recommended tilt and recline settings suitable to the particular wheelchair user based on his or her specific profile.

Figure 14:
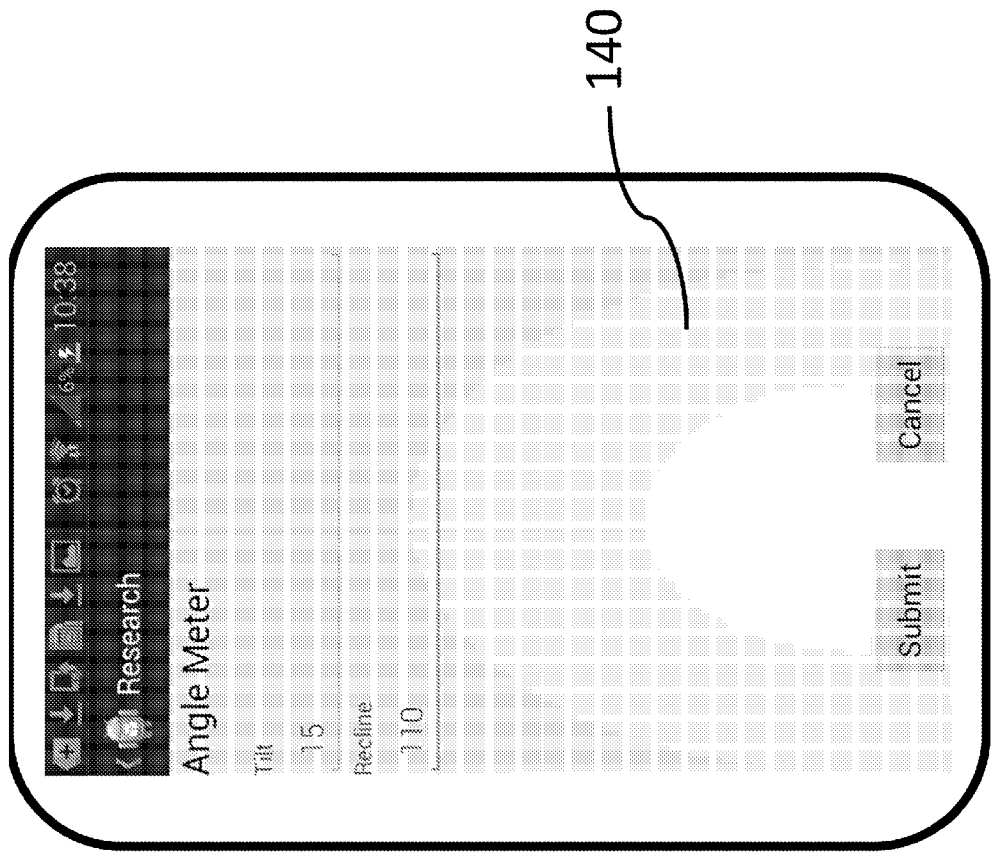
FIG. 14 is a non-limiting diagram showing an exemplary screenshot for "1: Set the target tilt and recline angles (e.g., 15 tilt/110 recline)" as the first step depicted in FIG. 13.

FIG. 14 is a non-limiting diagram showing an exemplary screenshot of the user interface implemented as an element in the process for determining proper adjustment of tilt and recline settings as determined by the present invention. A screenshot for "1: Set the target tilt and recline angles (e.g., 15 tilt/110 recline)" is shown as the first step depicted in FIG. 13.

Figure 15:
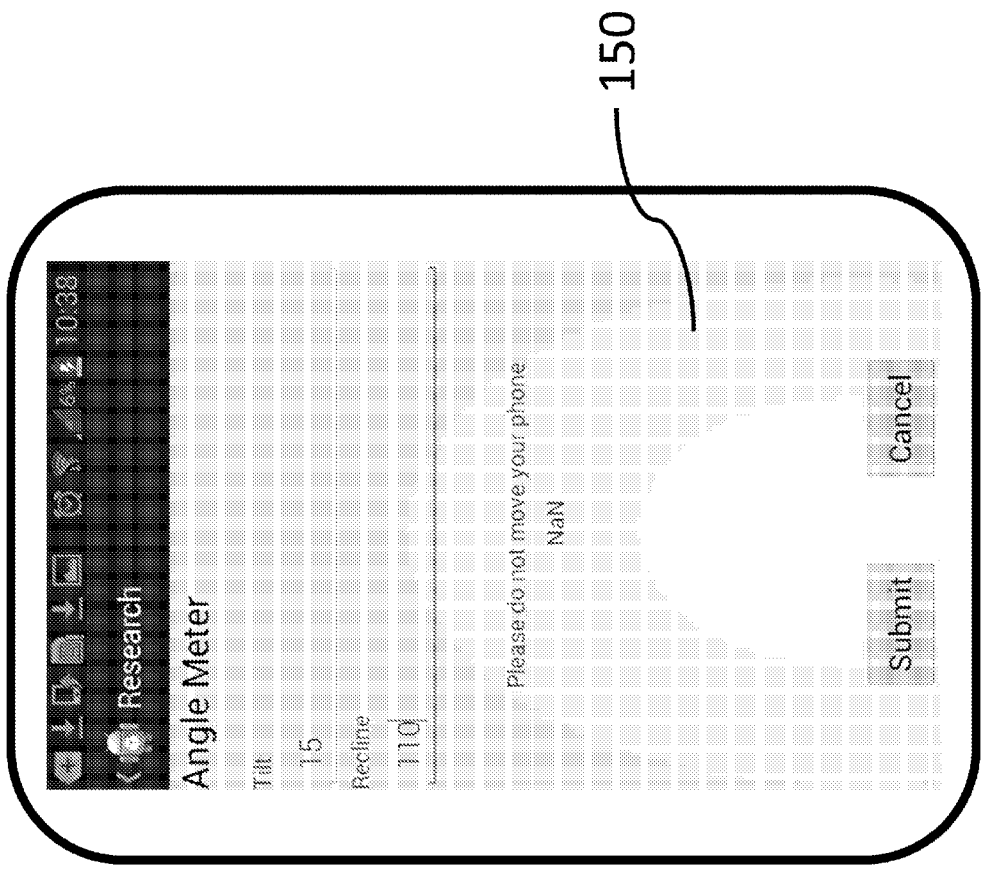
FIG. 15 is a non-limiting diagram showing an exemplary screenshot for "5: Alert the user to stay still for 5 seconds" as the fifth step depicted in FIG. 13.

FIG. 15 is a non-limiting diagram showing an exemplary screenshot of the user interface implemented as an element in the process for determining proper adjustment of tilt and recline settings as determined by the present invention. Actionable aural guidance is provided to ask the user to stay still for a period of time (e.g., 5 seconds) so that the smart device application can accurately measure the initial upright position. An exemplary screenshot for "5: Alert the user to stay still for 5 seconds" is shown as the fifth step depicted in FIG. 13.

Figure 16:
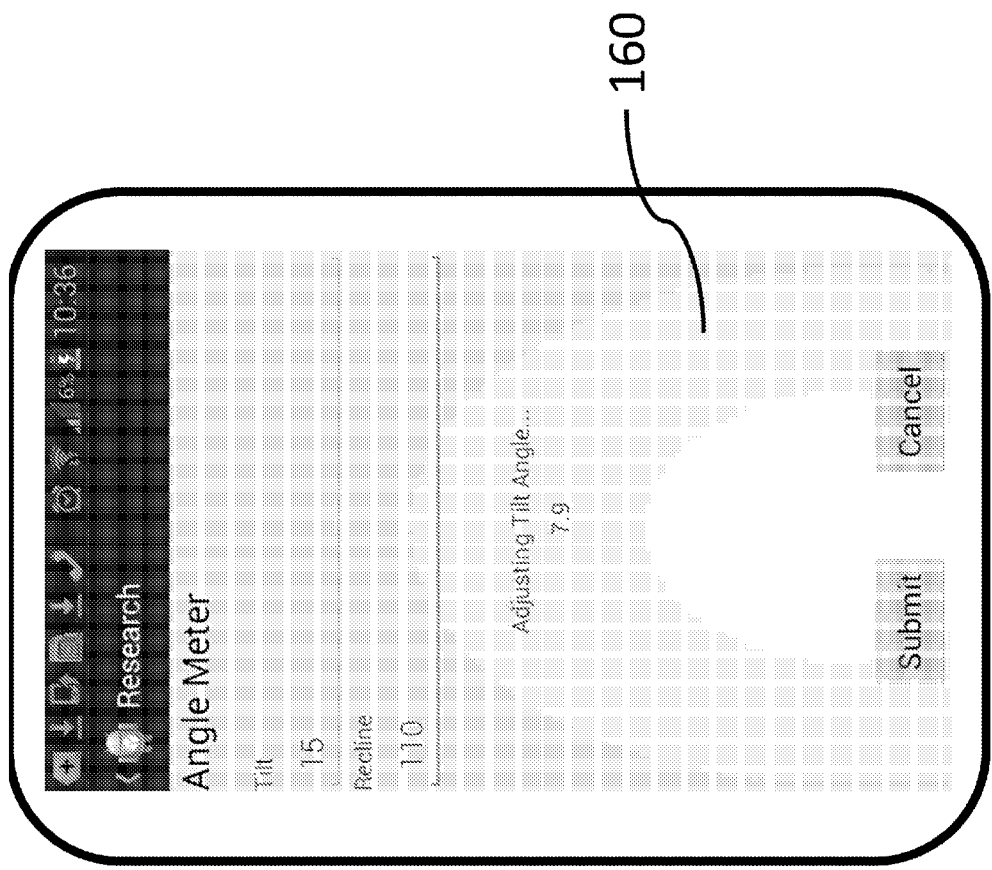
FIG. 16 is a non-limiting diagram showing an exemplary screenshot of the display on the user interface while the user adjusts the tilt angle as the seventh step depicted in FIG. 13.

FIG. 16 is a non-limiting diagram showing an exemplary screenshot of the user interface implemented as an element in the process for determining proper adjustment of tilt and recline settings as determined by the present invention. A screenshot of the display on the user interface while the user adjusts the tilt angle is shown as the seventh step depicted in FIG. 13.

Figure 17:
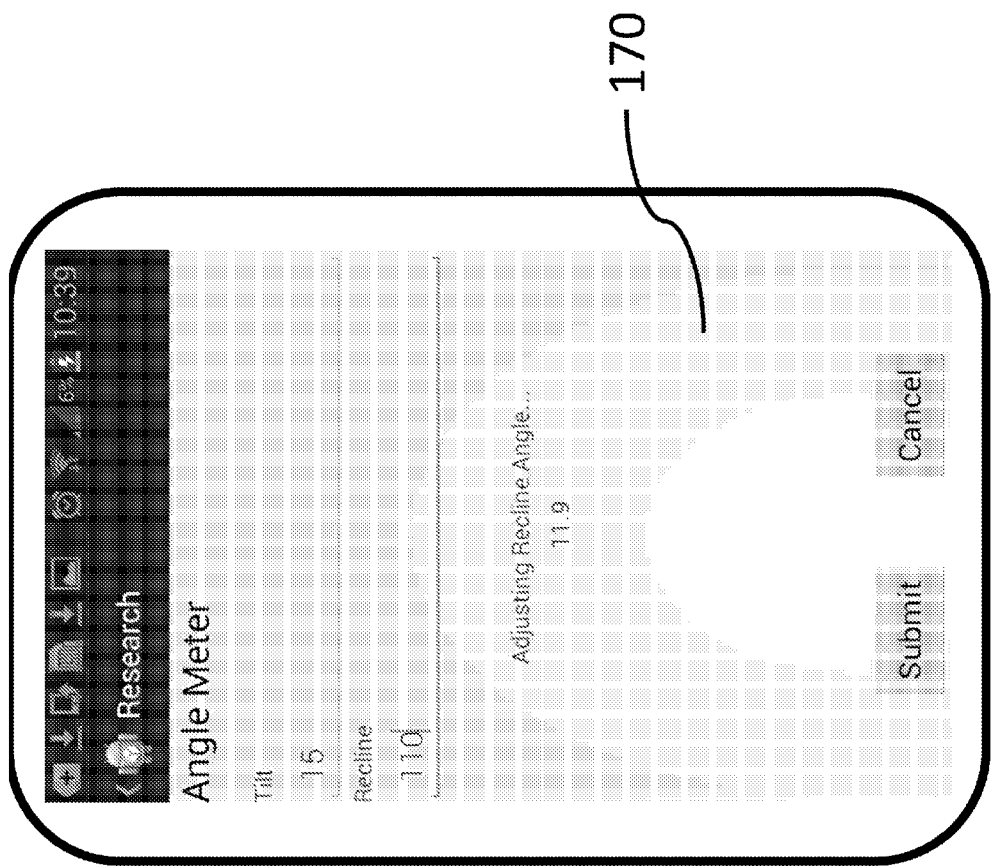
FIG. 17 is a non-limiting diagram showing an exemplary screenshot of the display on the user interface while the user adjusts the recline angle as the tenth step depicted in FIG. 13.

FIG. 17 is a non-limiting diagram showing an exemplary screenshot of the user interface implemented as an element in the process for determining proper adjustment of tilt and recline settings as determined by the present invention. A screenshot of the display on the user interface while the user adjusts the recline angle, is shown as the tenth step depicted in FIG. 13.

Figure 18:
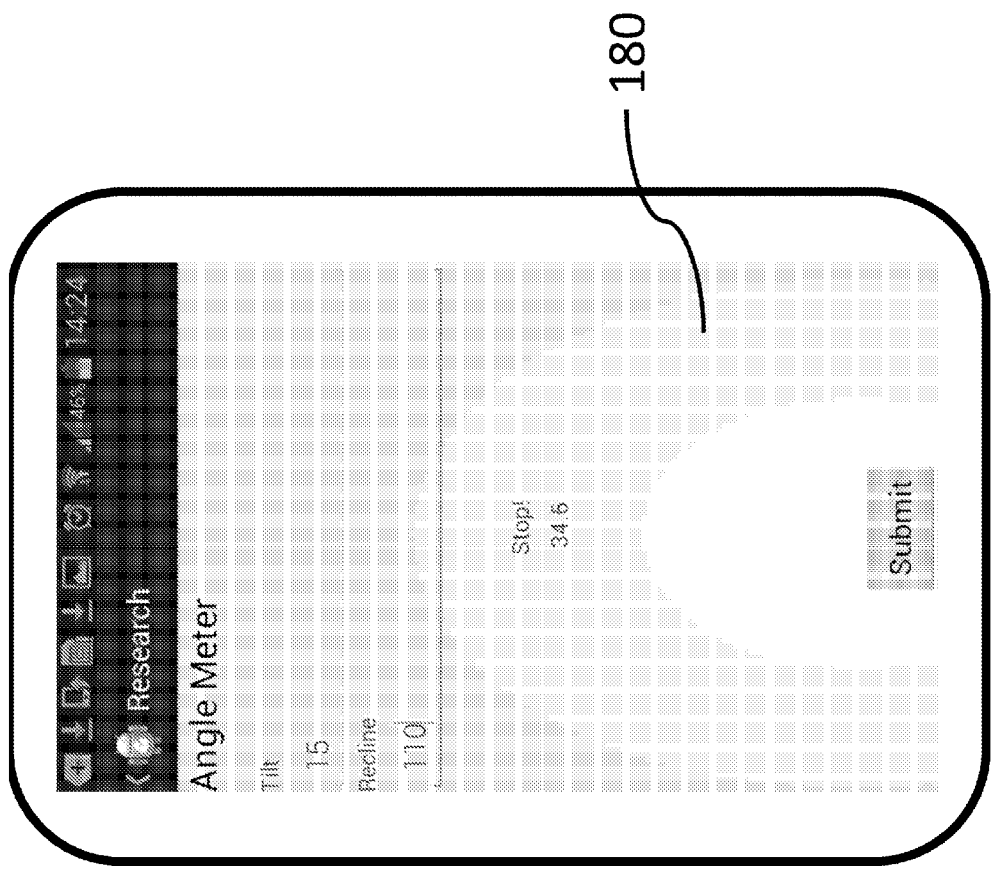
FIG. 18 is a non-limiting diagram showing an exemplary screenshot of the display on the user interface while the smartphone application uses voice alerts to tell the user that the target recline angle has been reached as the eleventh step depicted in FIG. 13.

FIG. 18 is a non-limiting diagram showing an exemplary screenshot of the user interface implemented as an element in the process for determining proper adjustment of tilt and recline settings as determined by the present invention. A screenshot of the display on the user interface is shown as the eleventh step depicted in FIG. 13. Actionable aural guidance may be provided concomitantly to tell the user that the target recline angle has been reached.

Figure 19:
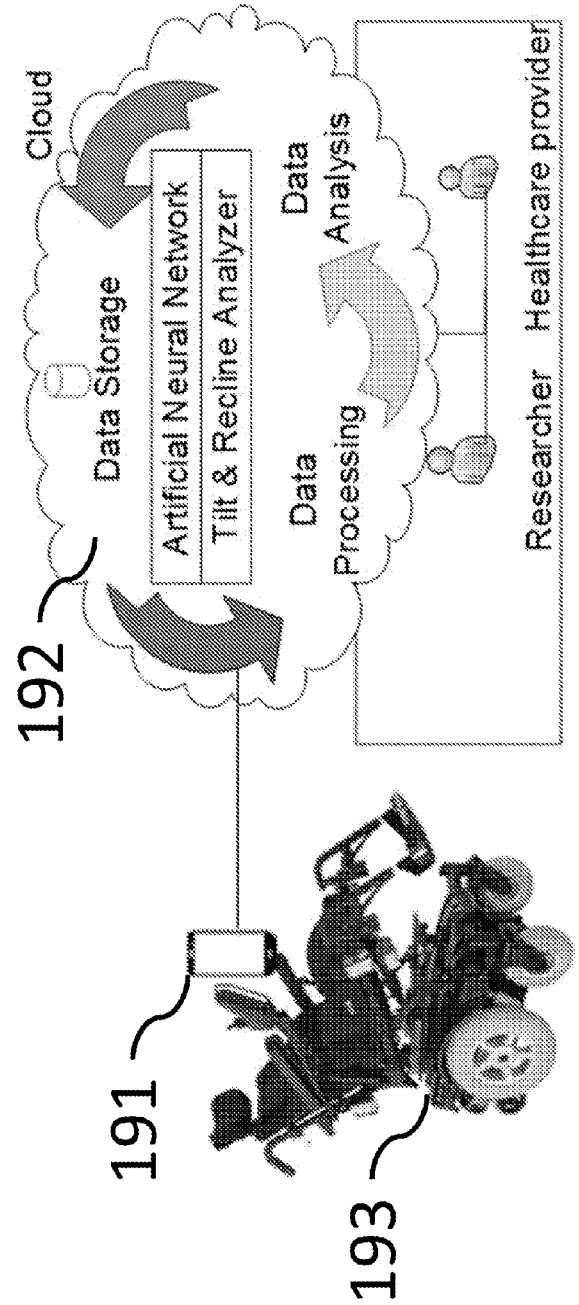
FIG. 19 is a non-limiting diagram showing the top level architecture of the mobile-cloud implementation of the present invention.

FIG. 19 is a non-limiting diagram showing the top level architecture of the mobile-cloud implementation of the present invention. An artificial neural network is shown implemented in the cloud, along with data processing and analysis. Researchers and healthcare providers are able to remotely access patient data through a secure and controlled interface.

In detail: Referring now to FIG. 1, a non-limiting schematic illustration of one embodiment of the present invention 10 shows one configuration of the process flow for a typical smartphone implementation of the present invention (i.e., the local version) 10. Users must create their profiles 11 before they can use the system (see FIG. 11a). A profile may include information comprising the user's age, gender, height, weight, body mass index, level of injury, completeness of injury, duration of injury, age at onset of SCI, whether he/she smokes, drinks alcohol, exercises, and/or has pressure ulcer history. The profile is stored locally in the smartphone. Then, the user can proceed to use the implemented smartphone application. The user has the options to update his/her profile 14, retrieve recommendations for wheelchair tilt & recline usage 15, and use the goniometer implemented in the smartphone to measure wheelchair tilt/recline angles 16. Note that the artificial neural networks (ANN) are implemented locally in the smartphone. The ANNs can provide the set of favorable tilt and recline settings and the best tilt and recline setting for individual users based on their profiles.

Referring now to FIG. 2, a non-limiting schematic illustration of one embodiment of the present invention 10 shows one configuration of the process flow for the mobile-to-cloud implementation of the present invention 10 (also see FIG. 19). Users must register 21 to create their profiles before they can login 22. The smartphone application provides the user interface that allows the users to register (i.e., create their own profiles. See FIG. 11a). A profile may include information comprising the user's age, gender, height, weight, body mass index, level of injury, completeness of injury, duration of injury, age at onset of SCI, whether he/she smokes, drinks alcohol, exercises, and/or has pressure ulcer history. In addition, the user needs to choose a user name and password. The profile is then stored in the cloud (see FIG. 19), i.e., the smartphone's communication capability (3G, 4G or WIFI) is used to transmit data to the cloud. If a user can provide a valid user name and password 23, he/she can proceed to use the implemented application operable and running on the smartphone. The user has the options to update his/her profile 24, retrieve recommendations for wheelchair tilt & recline usage 25, and use the goniometer implemented in the smartphone to measure wheelchair tilt/recline angles 26. Note that under the mobile-to-cloud configuration, the artificial neural network (ANN) is implemented in the cloud. The ANN can provide the set of favorable tilt and recline settings and the best tilt and recline setting for individual users based on a user's profile. Under the mobile-to-cloud configuration of the present invention 10, a single artificial intelligent module may be configured to serve a plurality of mobile users, who may use various mobile operating systems, such as iOS, Android, Windows, etc. In the mobile side, the users need to login 22 to the application by providing their user names/passwords. Then, the users may use the application in the same way as a user operating the local version of the present invention 10. The difference is that the information on the guidance of wheelchair tilt and recline usage is retrieved from the cloud. This difference is made transparent to the users. Hence, the users do not have to take care of the complex technical details directed to data storage and computation.

Referring now to FIG. 3, a non-limiting diagram is shown presenting the function of "retrieve wheelchair tilt & recline usage" 30 of the present invention 10 (see also 15 in FIGS. 1 and 25 in FIG. 2). Specifically, users can obtain a set of favorable incline angles including tilt and recline combinations 31 that can help reduce the risk of pressure ulcers. An overall picture of a user's favorable tilt and recline settings are presentable, along with choices to adjust seating positions. Users are also presented with the best tilt and recline settings 32 that can most effectively reduce risk of pressure ulcers. Users may select the option "retrieve optimal wheelchair tilt and recline setting". A third option is retrieving the optimal duration and frequency to perform wheelchair tilt and recline. Users may elect to retrieve information directed to how often (i.e., frequency) they should perform wheelchair tilt and recline functions and how long (i.e., duration) each time they should maintain at that tilt and recline setting 33. For example, guidance may be provided such as "perform tilt and recline every 15 minutes (i.e., frequency) and maintain the tilt and recline setting for at least 3 minutes (i.e., duration).

The preferable output includes (1) a range of tilt and recline angles that are favorable for pressure reduction for the user 31; (2) the optimal tilt and recline angles that are most effective in reducing the risk of pressure ulcers 32; and (3) the optimal frequency and duration to perform wheelchair tilt and recline functions 33.

Referring now to FIG. 4a, a non-limiting diagram is shown presenting a screen shot of a user interface 40 in a smartphone implementation of the present invention 10 (i.e., the mobile-to-cloud version). A user can choose "submit" 41 if he/she is an existing user. Otherwise, the user needs to register 42 (see FIG. 11a) before proceeding. All users' profiles are stored in the cloud (see FIG. 19). For an existing user, the smartphone application sends his/her user name and password (collected in FIG. 4a) to the cloud application of the present invention to verify the user's identity. Only valid users can use or gain access to the system. System responses are anticipated to at least user touch and voice commands.

Referring now to FIG. 4b, a non-limiting diagram is shown presenting a screen shot 43 of a user interface in a web implementation of the present invention 10. A user can choose "sign in" 44 if he/she is an existing user. Otherwise, the user needs to register 45 (see FIG. 11b) before proceeding. Under the web implementation, all users' profiles are stored in the cloud. For an existing user, the web application sends his/her user name and password (collected in FIG. 4b) to the cloud application of the present invention to verify the user's identity. Only valid users can use or gain access to the system. System responses are anticipated to at least user touch and voice commands.

Referring now to FIG. 4c, in a preferred implementation, the best known artificial neural network (ANN) is implemented for the present invention 10. ANN has a layered network structure 400, in which the processing units (i.e., neurons) are arranged in layers. The ANN in FIG. 4c consists of three layers, including the input layer 401, the hidden layer 402, and the output layer 403. Neurons in adjacent layers can communicate with each other by sending and receiving signals through the weighted connections. The input/output behavior of a neuron is defined by its internal activation function, which accumulates the input signals and then calculates the outputs. Once the network structure 400 is determined, the learning process proceeds in iterations by tuning the weights of connections using a training algorithm, such as the well-known back-propagation algorithm.

The network structure and weights of the ANN in the application are determined offline by using clinical research data on clinically recommended tilt and recline angles. Specifically, wheelchair users with spinal cord injury were recruited to participate in the research. A testing condition includes a five-minute sitting-induced ischemic period, i.e., the research participant sits in the upright position with no tilt or recline for 5 minutes, and a five-minute pressure relief period, i.e., the research participant sits in a clinically recommended tilt and recline setting for 5 minutes. The skin blood flow was measured throughout the test so that we can know whether a tilt and recline setting is favorable for increasing skin blood flow, which has been widely used to determine the efficacy of wheelchair seating conditions. Then, the skin blood flow data was used to train the ANN to predict tilt and recline settings for individual wheelchair users. Other position parameters may be incorporated as well, such as the elevating leg-rest function of a power wheelchair. The ANN in the invention is fully configurable through adjusting the network structure 400 and weights. The ANN can be replaced by other artificial intelligence techniques, namely, any classification, clustering, and regression techniques, such as support vector machine (SVM), C4.5 decision tree, random forest, etc. The present invention will support such transparency in changing the AI module.

Referring now to FIG. 5, a non-limiting diagram is shown presenting a top-level code structure 50 for a smart device application of the present invention 10 (i.e., the local version). The code structure 50 comprises the following modules: InitActivity 51, ClsTrainer 52, Main 50A, InputData 53, ResultTask 54, FragmentForm 55, FragmentFrequency 56, FragmentAngleMeter 57, IntentService.java 571, FragmentList 58, and FragmentResult 59.

InitActivity.java: This class 51 shows the welcome screen when the application is loading. It calls ClsTrainner 52 to train the classifiers in the backend. Once it finishes initializing classifiers, this activity class will transfer to the Main 50A activity class.

ClsTrainner.java: This class 52 is used to initialize a classifier and regression learner coded in the present invention. The classifier can classify whether a given tilt and recline setting is favorable for an individual with spinal cord injury (SCI) to reduce the risk of pressure ulcer. The regression learner can predict the extent of risk deduction for a given tilt and recline setting. This class runs in the backend as a thread when the application starts.

Main.java: The Main class 50A is the container for all the fragment classes in this application. It provides the overall layout of the application.

FragmentForm.java: This class 55 is used to provide the user interface to input data 53. Users can update their profiles (FIG. 1, 14, FIG. 2, 24) here. It can also call the classifier and regression modules to make new predictions with updated profiles.

FragmentFrequency.java: This class 56 shows to the users the optimal duration and frequency to perform the wheelchair tilt and recline functions. It invokes the daemon thread that is running in the backend to return the optimal duration and frequency to the user interface (UI) thread.

FragmentList.java: This class 58 provides a list of functions that is offered by the smartphone app. It redirects a user to the appropriate functions based on the user's choice.

FragmentResult.java: This class 59 includes the template of My Range, My Optimal, and My Test screens (shown on FIG. 10a) in the application. It shows the up-to-date prediction results obtained from the back-end thread.

InputData.java: This is a singleton class 53 that it has only a single instance in the memory. It contains all the data in this application. It acts as a data store in this application. The trained functions (classifier and regression) as well as user inputs are all stored in this class.

ResultTask.java: The ResultTask class 54 is running in the backend as a daemon thread. Its functionality is to make predictions based on a user's profile (FIG. 1, 14, FIG. 2, 24). This class also answers other requests, such as whether a particular tilt and recline setting is favorable for the user, and returns the result to the UI thread.

FragmentAngleMeter.java: This class 57 provides the goniometer function. It reads the accelerometer sensor in the smartphone and calculates the current angle of the phone orientation for the user. This class provides a novel algorithm to measure wheelchair tilt and recline (TR) angles by using the accelerometer in a smartphone. Specifically, the position of a smartphone is modeled with a vector $v=(\alpha_x, \alpha_y, \alpha_z)$, which represents accelerations in three axes measured by the accelerometer. When the tilt or recline stabilizes to a new angle, accelerations in three axes will change due to the decomposition of the gravity along the new angle of the phone. Then, we utilize the dot product property to calculate angle changes between two vectors (positions):

$$v_1 \cdot v_2 = |v_1| \times |v_2| \times \cos\theta \quad (1)$$

Or equivalently, $$\theta = \arccos(v_1 \cdot v_2 / |v_1| \times |v_2|) \qquad (2)$$

Hence, no matter how the smartphone is positioned, the TR angle θ between two vectors can be measured. In addition, this class employs the novel text-to-speech technique (see class IntentService.java), which enables the system to use voice alerts to guide wheelchair users for proper TR usage.

IntentService.java: This class 571 implements the Android text-to-speech listener and initializes the text-to-speech function for the subsequent usage.

Referring now to FIG. 6, a non-limiting diagram is shown presenting a top-level data flow for a Web based configuration 60 of the present invention 10. The code structure for a Web based configuration 60 comprises the following modules: Index Page 61 (index.html), Register 611 (SignInServlet), Sign in 612 (SignInServlet), User Welcome Page 62 (welcome.jsp), Profile Page 621 (profile.jsp), Update Profile 6211 (UpdateUserServlet), Check Angle Page 622 (check.jsp), Check Angles 6221 (CheckAnglesServlet), Range of Angles Page 623 (result.jsp), Optimal Angle Page 624 (optimal.jsp), Duration and Frequency Page 625 (duration.jsp), Admin User List Page 63 (admin.jsp), Delete User 631 (DeleteUserServlet), Edit User Page 632 (edituser.jsp), Edit User 64 (UpdateUserServlet), and Create New User 65 (UpdateUserServlet).

Index Page 61 (index.html): Index page 61 is the first web page that a user can access. It provides options for registered users to sign in and for unregistered users to register.

Register 611 (SignInServlet): It is a Java Servlet that is invoked by index.html and allows unregistered users to register and create their own user names and passwords. A Java servlet is a class that is used to extend the functionality of the cloud.

Sign in 612 (SignInServlet): It is a Java servlet used by index.html when to sign in and register users given a username and password.

User Welcome Page 62 (welcome.jsp): It is the welcome page after a user successfully signs in the system.

Profile Page 621 (profile.jsp): This page allows users to create their own profiles including their demographic attributes, neurological information, and pressure ulcer history, etc.

Update Profile 6211 (UpdateUserServlet): It is a servlet class that is invoked by profile.jsp to update the user's profile.

Check Angle Page 622 (check.jsp): This page gives a user the option to check whether a particular wheelchair tilt and recline setting will be favorable for the individual user to reduce pressure ulcer's risk.

Check Angles 6221 (CheckAnglesServlet): It is a servlet class that is invoked by check.jsp to check whether a particular wheelchair tilt and recline setting will be favorable for the individual user to reduce pressure ulcer risk.

Range of Angles Page 623 (result.jsp): This page shows the range of tilt and recline angles that are favorable for reducing pressure ulcers' risk.

Optimal Angle Page 624 (optimal.jsp): This page shows the optimal wheelchair tilt and recline settings that may most effectively reduce risk of pressure ulcers.

Duration and Frequency Page 625 (duration.jsp): This page illustrates the optimal duration and frequency to perform wheelchair tilt and recline functions. For example, the user should perform wheelchair tilt and recline functions every 15 minutes (i.e., frequency) and each time the user should maintain that setting for 3 minutes (i.e., duration).

Admin User List Page 63 (admin.jsp): This is a page designed for administrators, who will maintain users, including "add", "edit", and "delete" users.

Delete User 631 (DeleteUserServlet): It is a Java servlet used by admin.jsp when an administrator attempts to delete an application user.

Edit User Page 632 (edituser.jsp): This is a web page that invokes Servlets to add a new user or update an existing user.

Edit User 64 (UpdateUserServlet): It is a Java servlet used by admin.jsp when an administrator attempts to edit a user's information.

Create New User 65 (UpdateUserServlet): The same UpdateUserServlet can also be used to create a new user.

Referring now to FIG. 7, a non-limiting diagram is shown presenting a top-level control flow of the present invention 10 for mobile-to-cloud configuration using the Android operating system. The code structure 70 includes: Login Screen 71, Register 72, Datastore 721, Sign In 73, User Menu Screen 701 (MenuActivity), Profile Screen 74 (FragmentForm), Check Angle Page 75 (FragmentCheck), Range of Angles Page 76 (FragmentResult), Optimal Angles Page 77 (FragmentOptimal), Duration and Frequency Page 78 (FragmentFrequency), and Goniometer 79 (FragmentAngleAdjustment).

Login Screen 71 (LoginActivity): It is the starting Android activity that calls register and signin methods and redirects user to the MenuActivity 701 if the user name and password are verified successfully. Activity is an Android term that represents a function that a user can perform.

Register 72: It invokes the Datastore class (Datastore.register function) that interacts with the Google App Engine datastore to store new user's information (see FIG. 19).

Datastore 721: This class interacts with the Google App Engine datastore service and is used by both the mobile endpoints and java servlets.

Sign In 73: It invokes the Datastore class (Datastore.signin function) that interacts with the Google App Engine datastore to validate the user's information (see FIG. 19).

User Menu Screen 701 (MenuActivity): It is the main activity that shows the main menu of the system. It consists of the currently selected fragment and a navigation list for changing fragments. A fragment is an Android term that represents a portion of the user interface.

Profile Screen 74 (FragmentForm): It is a fragment that consists of the input fields for user information. Once the button at the bottom of the fragment is pressed, the given information is then updated 741 to the datastore in the cloud (see FIG. 19).

Check Angle Page 75 (FragmentCheck): It is a fragment that determines if the given tilt and recline angles 751 are in the ranges provided by the artificial neural network (see FIG. 19).

Range of Angles Page 76 (FragmentResult): It is a fragment that displays a list of ranges provided by the artificial neural network (see FIG. 19). These ranges are favorable tilt and recline combinations that can help reduce the risk of pressure ulcers.

Optimal Angles Page 77 (FragmentOptimal): It is a fragment that displays the optimal angles of wheelchair tilt and recline provided by the artificial neural network (see FIG. 19).

Duration and Frequency Page 78 (FragmentFrequency): It is a fragment used to check the duration and frequency that the user should perform wheelchair tilt and recline functions. For example, the user should perform wheelchair tilt and recline functions in every 15 minutes (i.e., frequency) and each time the user should maintain that position for 3 minutes (i.e., duration).

Goniometer 79 (FragmentAngleAdjustment): It is a fragment used to display the current angle of the phone. It reads the accelerometer sensor in the smartphone and calculates the current angle of the phone orientation for the user. A desired angle can be set by using the device's menu button. The background of this fragment will turn greener the closer the current angle is to the desired angle.

Referring now to FIG. 8a, a non-limiting diagram is shown presenting a class diagram 80 for GAE (cloud) configuration of the present invention 10 where the classes are used to compute personalized guidance on wheelchair tilt and recline, and interact with the mobile and web applications. The code structure includes: ApplicationUser 81, BloodFlowCore 82, BloodFlowResult 83, Range 84, UserEndpoint 85, CheckAnglesServlet 86, SignInServlet 87, ResultEndpoint 88, UpdateUserServlet 89, DeleteUserServlet 810, SignOutServlet 811, MLP 812, LinearUnit 816, NeuralEnd 817, and NeuralConnection 818. ApplicationUser 81: consists of all user fields and represents the entity structure stored in the Google App Engine (GAE) datastore.

BloodFlowCore 82: contains methods for interacting with the WEKA API, which is an open source data mining platform and returning the BloodFlowResult object. This is where the artificial neural network is built and angles are returned.

BloodFlowResult 83: contains all output results needed and eventually displayed to the user, including a list of tilt and recline ranges, the optimal angles, and duration and frequency.

Range 84: is a class used to hold one set of tilt and recline ranges.

UserEndpoint 85: this Endpoint class manipulates ApplicationUser entities in the datastore by calling the Datastore class methods. Endpoint classes are located in the GAE source code and are annotated to be generated into an API to be used with Android.

CheckAnglesServlet 86: is a servlet class that checks whether a particular wheelchair tilt and recline setting will be favorable for the individual user to reduce pressure ulcer's risk.

SignInServlet 87: is a Java servlet used when to sign in and register users given a username and password.

ResultEndpoint 88: this endpoint creates a BloodFlowResult object to store results from the runBloodFlowCore method. Endpoint classes are located in the GAE source code and are annotated to be generated into an API to be used with Android.

UpdateUserServlet 89: is a Java servlet used when an administrator attempts to edit a user's information.

DeleteUserServlet 810: is a Java servlet used when an administrator attempts to delete an application user.

SignOutServlet 811: This class provides the sign out function in the web application.

MLP.java 812: The MLP class is customized by adding getNumWeights( ), importWeights( ), and exportWeights( )methods. These methods allow us to reconstruct ANN if the network structure and weights are provided.

MLP 812, LinearUnit 816, NeuralEnd 817, and NeuralConnection 818 are obtained from WEKA, which is an open source platform for data mining. These classes are used to model the artificial neural network. LinearUnit 816, NeuralEnd 817, and NeuralConnection 818 are used without any customizations.

Referring now to FIG. 8b, a non-limiting diagram is shown presenting a class diagram 80 for GAE (cloud) configuration of the present invention 10 where the classes are used to store the tilt and recline usage information (the time when the user performs the tilt and recline functions, the angles of the tilt and recline, etc.) The code structure includes: AngleData 813, DataManager 814, and EMF 815.

AngleData 813: is the data type class that models tilt and recline angle data, which is sent from the mobile client.

DataManager 814: is the class that handles the communication between the client and Google datastore.

EMF 815: EntityManagerFactory helps communication between the Google datastore and the application.

Referring now to FIG. 9, a non-limiting diagram is shown presenting a class diagram 90 for a mobile configuration of the present invention 10 using the Android operating system (complementing FIG. 7). The code structure includes: LoginActivity 91, MenuActivity 92, FragmentForm 921, FragmentCheck 922, FragmentResult 923, FragmentOptimal 924, FragmentFrequency 925, FragmentAngleAdjustment 926, FragmentList 927, Datastore 93, UserEndpoint 94, ResultEndpoint 95, and BloodFlowCore 96.

LoginActivity 91: it is the starting Android activity that calls register and signin methods and redirects user to the MenuActivity 92 if the user name and password are verified successfully. Activity is an Android term that represents a function that a user can perform.

MenuActivity 92: it is the main activity that shows the main menu of the system. It consists of the currently selected fragment and a navigation list for changing fragments. A fragment is an Android term that represents a portion of the user interface.

FragmentForm 921: It is a fragment that consists of the input fields for user information. Once the button at the bottom of the fragment is pressed, the given information is then updated to the datastore in the cloud. A fragment is an Android term that represents a portion of the user interface.

FragmentCheck 922: It is a fragment that determines if the given tilt and recline angles are in the ranges provided by the artificial neural network.

FragmentResult 923: It is a fragment that displays a list of ranges provided by the artificial neural network. These ranges are favorable tilt and recline combinations that can help reduce the risk of pressure ulcers.

FragmentOptimal 924: It is a fragment that displays the optimal angles of wheelchair tilt and recline provided by the artificial neural network.

FragmentFrequency 925: It is a fragment used to check the duration and frequency that the user should perform wheelchair tilt and recline functions. For example, the user should perform wheelchair tilt and recline functions every 15 minutes (i.e., frequency) and each time the user should maintain that setting for 3 minutes (i.e., duration).

FragmentAngleAdjustment 926: It is a fragment used to display the current angle of the wheelchair (tilt or recline). It reads the accelerometer sensor in the smartphone and calculates the current angle of the phone orientation for the user. A desired angle can be set by using the device's menu button. The background of this fragment will turn greener the closer the current angle is to the desired angle.

FragmentList 927: is a fragment that provides a list of functions that is offered by the smartphone app. It redirects a user to the appropriate functions based on the user's choice.

Datastore 93: this class is used by the mobile endpoints to interact with the Google App Engine datastore to manipulate data.

UserEndpoint 94: this Endpoint class manipulates ApplicationUser entities in the datastore by calling the Datastore class methods. Endpoint classes are located in the GAE source code and are annotated to be generated into an API to be used with Android.

ResultEndpoint 95: this endpoint creates a BloodFlowResult object to store results from the runBloodFlowCore method. Endpoint classes are located in the GAE source code and are annotated to be generated into an API to be used with Android.

BloodFlowCore 96: contains methods for interacting with the WEKA API, which is an open source data mining platform and returning the BloodFlowResult object. This is where the artificial neural network is built and angles are returned.

FIG. 10*a* is a non-limiting diagram showing a screen shot of a smartphone implementation of the present invention 10 providing a user interface 101 to access system functions. Both the local mobile version and the mobile-to-cloud version may have the same interface as shown in FIG. 10*a*. System responses are anticipated and implemented to include at least user touch and voice commands. Audio recitation and response for visually impaired individuals may be provided by the present invention 10. User touch, voice activation and audio recitation functions are generally programmable and operable on industry standard smart devices, such as various device models of iPhone, iPad, Samsung Galaxy, and HP tablets, running operating systems such as Android, iOS, and Windows, where such devices include an accelerometer. Implementation on any such mobile device having the minimum function set as described herein is anticipated.

FIG. 10*b* a non-limiting diagram showing a screen shot of a web-based implementation of the present invention 10 providing a user interface 102 to access system functions. System responses are anticipated and provided in the present invention 10 to include at least user touch and voice commands. Audio recitation and response for visually impaired individuals may also be provided by the present invention 10.

FIG. 11*a* is a non-limiting diagram showing a screen shot of a smartphone implementation of the present invention 10 providing a user interface 110 to enter demographic attributes. System responses are anticipated and provided in the present invention 10 to include at least user touch and voice commands. Audio recitation and response for visually impaired individuals is anticipated and provided by the present invention 10. User touch, voice activation and audio recitation functions are generally programmable and operable on industry standard smart devices, such as various device models of iPhone, iPad, Samsung Galaxy, and HP tablets, running operating systems such as Android, iOS, and Windows, where such devices include an accelerometer. Any such device having the minimum function set as described herein is anticipated.

FIG. 11*b* is a non-limiting diagram showing a screen shot of a web-based implementation of the present invention 10 providing a user interface 112 to enter demographic attributes. System responses are anticipated and provided in the present invention 10 to include at least user touch and voice commands. Audio recitation and response for visually impaired individuals is anticipated and provided by the present invention 10.

FIG. 12*a* is a non-limiting diagram showing a screen shot of a smartphone implementation of the present invention 10 providing a user interface 120 to display favorable tilt and recline angles. System responses are anticipated and provided in the present invention 10 to include at least user touch and voice commands. Audio recitation and response for visually impaired individuals is anticipated and provided by the present invention 10. User touch, voice activation and audio recitation functions are generally programmable and operable on industry standard smart devices, such as various device models of iPhone, iPad, Samsung Galaxy, and HP tablets, running operating systems such as Android, iOS, and Windows, where such devices include an accelerometer. Implementation on any such device having the minimum function set as described herein is anticipated.

FIG. 12*b* is a non-limiting diagram showing a screen shot of a web-based implementation of the present invention 10 providing a user interface 122 to display favorable tilt and recline angles. System responses are anticipated in the present invention 10 to include at least user touch and voice commands. Audio recitation and response for visually impaired individuals is anticipated and provided by the present invention 10.

FIG. 12*c* is a non-limiting diagram showing a screen shot of a smartphone implementation of the present invention 10 providing a user interface 124 to display the best tilt and recline angle for the user. System responses are anticipated and provided in the present invention 10 to include at least user touch and voice commands. Audio recitation and response for visually impaired individuals is anticipated and provided by the present invention 10. User touch, voice activation and audio recitation functions are generally programmable and operable on industry standard smart devices, such as various device models of iPhone, iPad, Samsung Galaxy, and HP tablets, running operating systems such as Android, iOS, and Windows, where such devices include an accelerometer. Implementation on any such device having the minimum function set as described herein is anticipated.

FIG. 12*d* is a non-limiting diagram showing a screen shot of a web-based implementation of the present invention 10 providing a user interface 126 to display the best tilt and recline angle for the user. System responses are anticipated in the present invention 10 to include at least user touch and voice commands. Audio recitation and response for visually impaired individuals is anticipated and provided by the present invention 10.

FIG. 13 is a non-limiting diagram showing the measurement and notification process 130 for determining proper adjustment of tilt and recline settings as determined by the present invention 10. Measurement, display, and auditory notification of tilt and recline angles are accomplished in substantially real-time as a user adjusts tilt and recline settings on a wheelchair. Actionable aural guidance is provided to enable the user to achieve recommended tilt and recline settings suitable to the particular wheelchair user based on his or her specific profile.

The present invention 10 can benefit all wheelchair users, who use a wheelchair with either a tilt or both tilt and recline functions. Both power and manual wheelchair users can benefit from this and other functions of the present invention 10. Healthcare providers and researchers will benefit from the present invention 10, as well. If they use the tilt and recline guidance provided by the present invention 10, the guidance will be automatically provided as inputs to the measurement and notification process 130 implemented in source code and operable on a mobile device. If the health providers and researchers do not use the personalized guidance, the present invention 10 will allow them to input alternative tilt and recline (TR) guidelines (see FIG. 14) to the measurement and notification process 130 so that the wheelchair users can follow those guidelines.

As shown in FIG. 13, in step 1 the wheelchair user uses the goniometer to set the target tilt and recline angles (e.g., 15° tilt/110° recline) and then click the "Submit" button (see FIG. 14). If the wheelchair only has the tilt function, the user only needs to provide the tilt angle.

In step 2, the goniometer asks the wheelchair user to adjust the wheelchair to the upright position (i.e., no tilt or recline). As shown in FIG. 13, the goniometer will use the novel voice alert technique of the present invention 10 to guide the user. For example, the voice alert may recite the non-limiting script "Please make sure that your wheelchair is in the upright position. Touch anywhere on the screen when you are ready!"

In step 3, the wheelchair user adjusts the wheelchair to the upright position following the voice guidance.

In step 4, the wheelchair user touches the screen of the smartphone after the wheelchair has been adjusted to the upright position.

In step 5, the goniometer asks the user to sit still so that the goniometer can record the initial position of the smartphone. This step is needed to ensure the precision of angle calculation.

Voice alert is used to guide the user. For example, the voice alert may recite the non-limiting script "Please do not move your phone for five seconds." As shown in FIG. 15, the goniometer may also show the message on the screen.

In step 6, the goniometer may be configured to ask the user to adjust the tilt angle by using a voice alert. For example, the voice alert may recite the non-limiting script "You may now adjust your position. Please adjust your tilt to 15 degrees."

In step 7, the wheelchair user starts to adjust the tilt angle as instructed by the voice alert. In the meantime, the goniometer will measure and display the current tilt angle on the screen of the smartphone as shown in FIG. 16.

In step 8, if the target tilt angle has been reached, the goniometer may be configured to ask the wheelchair user to stop with the voice alert. For example, the voice alert may recite the non-limiting script "Please stop!"

In step 9, the goniometer may be configured to ask the wheelchair user to adjust the recline angle by using the voice alert. For example, the voice alert may recite the non-limiting script "Please adjust your Recline to 110 degrees."

In step 10, the wheelchair user starts to adjust the recline angle. In the meantime, the goniometer will measure and display the current recline angle on the screen of the smartphone as shown in FIG. 17.

In step 11, if the target recline angle has been reached, the goniometer of the present invention may be configured to use an aural instruction where the user may be asked with the voice alert to stop. For example the voice alert may recite the non-limiting script "Please stop! You are now in your target position." In the meantime, the goniometer will also show the final angle and the stop message on the screen of the smartphone as shown in FIG. 18. Note that 90° of recline represents no recline. Hence, for 15° tilt and 110° recline, the final angle should be 15°+(110°−90°)=35°. The present invention considers the lag that occurs when the user hears the voice alert and then stops adjusting the wheelchair position. The present invention calculates the anticipated time to reach the target angle based on the angular speed of wheelchair positioning adjustment. It alerts the user to stop ahead of the anticipated time to compensate the lag.

FIG. 14 is a non-limiting diagram showing an exemplary screenshot of the user interface 140 implemented as an element in the process for determining proper adjustment of tilt and recline settings as determined by the present invention 10. A screenshot for "1: Set the target tilt and recline angles (e.g., 15 tilt/110 recline)" is shown as the first step depicted in FIG. 13. User instructions and alerts displayed may be accompanied by aural instructions.

FIG. 15 is a non-limiting diagram showing an exemplary screenshot of the user interface 150 implemented as an element in the process for determining proper adjustment of tilt and recline settings as determined by the present invention 10. A screenshot for "5: Alert the user to stay still for 5 seconds" is shown as the fifth step depicted in FIG. 13. User instructions and alerts displayed may be accompanied by aural instructions.

FIG. 16 is a non-limiting diagram showing an exemplary screenshot of the user interface 160 implemented as an element in the process for determining proper adjustment of tilt and recline settings as determined by the present invention 10. A screenshot of the display on the user interface while the user adjusts the tilt angle is shown as the seventh step depicted in FIG. 13. User instructions and alerts displayed may be accompanied by aural instructions.

FIG. 17 is a non-limiting diagram showing an exemplary screenshot of the user interface 170 implemented as an element in the process for determining proper adjustment of tilt and recline settings as determined by the present invention 10. A screenshot of the display on the user interface while the user adjusts the recline angle is shown as the tenth step depicted in FIG. 13.

FIG. 18 is a non-limiting diagram showing an exemplary screenshot of the user interface 180 implemented as an element in the process for determining proper adjustment of tilt and recline settings as determined by the present invention 10. A screenshot of the display on the user interface 180 is shown as the eleventh step depicted in FIG. 13. This screenshot occurs when the user has adjusted to the target recline setting. Hence, the wheelchair has been in the target tilt and recline setting. To let user know that the target setting has been reached, the actionable aural guidance is provided to alert the user.

FIG. 19 is a non-limiting diagram showing the top level architecture of the mobile-cloud implementation of the present invention. An artificial neural network is shown implemented in the cloud, along with data processing and analysis. Researchers and healthcare providers are able to remotely access patient data through a secure and controlled interface. The present invention 10 includes a mobile subsystem 191 and a cloud subsystem 192. Specifically, a mobile computing-based subsystem 191 is provided, which uses mobile devices (e.g., smartphones) to manage personal profile, retrieve personalized guidance on wheelchair tilt and recline (TR) usage, measure wheelchair 193 TR angles, and transmit TR usage data. Smartphones provide an ideal platform for implementing the present invention 10 due to the ubiquity of smartphones, their ever-increasing power, and rich set of sensors, such as the accelerometer. The present invention 10 provides a novel algorithm to measure wheelchair 193 TR angles (incline angles) by using the accelerometer in a smartphone. Specifically, the position of a smartphone is modeled with a vector $v=(\alpha_x, \alpha_y, \alpha_z)$, which represents accelerations in three axes measured by the accelerometer. When the tilt or recline stabilizes to a new angle, accelerations in three axes will change due to the decomposition of the gravity along the new angle of the phone. Then, the present invention utilizes the dot product property to calculate angle changes between two vectors (positions):

$$v_1 \cdot v_2 = |v_1| \times |v_2| \times \cos\theta \quad (1)$$

Or equivalently, $$\theta = \arccos(v_1 \cdot v_2 / |v_1| \times |v_2|) \quad (2)$$

Hence, no matter how the smartphone is positioned, the TR angle θ between two vectors can be measured. In addition, the mobile subsystem 191 employs the novel text-to-speech technique, which enables the system to use voice alerts to guide wheelchair users for proper TR usage.

The present invention 10 provides a cloud computing-based subsystem 192 that can provide personalized guidance on wheelchair tilt and recline usage using the artificial neural network, and process, store, and analyze wheelchair 193 TR usage data. This subsystem employs the cloud computing paradigm, which can provide virtually unlimited resources for computation and data storage. Based on the longitudinal TR usage data, the present invention 10 may be used to provide operational applications for mobile devices to evaluate whether wheelchair users adjust enough TR angles to relieve seating pressure and whether they frequently reposition themselves by performing TR functions. The present invention 10 may be used to provide a novel machine-learning approach to analyze historical data of an individual wheelchair user, and assess his or her pressure ulcer (PU) risks correspondingly.

The present invention 10 may use the Google App Engine (GAE) as the cloud computing platform. GAE is managed by Google and provides a platform for developing and hosting web applications. Note that other techniques may be used to replace GAE. Essentially, there are currently three options: (1) continue to use commercial cloud computing platforms, such as Google App Engine, Microsoft Azure, Amazon EC2, etc.; (2) set up a dedicated private cloud computing platform; or (3) use a traditional web server as the data management and computation platform. Other options may emerge in the future and are anticipated as possible web development and hosting solutions to support implementation of various features of the present invention.

The combination of mobile and cloud computing can yield a balanced and integrated system, in which the mobile subsystem 191 will collect user's information, display personalized guidance on TR usage, control the sensor, measure wheelchair TR angles, and transmit TR usage data to the cloud, while the cloud subsystem 192 will handle the subsequent data management and analysis. Therefore, the present invention 10 provides a practical way to improve wheelchair 193 TR usage and capture longitudinal TR usage data among wheelchair users The mobile application of the present invention 10 may be implemented for any mobile operating system, including the mainstream mobile operating systems, such as Google Android, Apple iOS, and Microsoft Windows. To use the mobile application provided by the present invention 10, the user needs to download it from an accessible public source where it may be made available, such as Google Play, Apple Store, or Windows App Store depending on the mobile operating systems they use.

Additional Embodiments Of The Present Invention

Preferred embodiments of the present invention may comprise generating personalized adjustment parameters directed to positioning and control of seating configurations in both commercial and private automotive vehicles, including trucks and passenger cars. Outcome objectives may reflect both safety and comfort. A smartphone implementation providing a user interface to display at least current position and shape parameters and send related control parameters to powered, adjustable seats is anticipated. System responses are anticipated to at least user touch and voice commands. Audio recitation and response is anticipated. User touch, voice activation and audio recitation functions are generally programmable and operable on industry standard smart devices, such as various device models of iPhone, iPad, Samsung Galaxy, HP tablets, Google glass, iWatch, etc, running on operating systems such as Android, iOS, and Windows, where such devices include an accelerometer. Any such mobile device having the minimum function set as described herein is anticipated. Implementation using on-board devices installed as vehicle equipment is also anticipated.

Preferred embodiments of the present invention may comprise generating personalized adjustment parameters directed to positioning and control of seating configurations in aircraft including both crew and passenger seating. Outcome objectives may reflect both safety and comfort. A smartphone implementation providing a user interface to display at least current position and shape parameters and send related control parameters to powered, adjustable seats is anticipated. System responses are anticipated to at least user touch and voice commands. Audio recitation and response is anticipated. User touch, voice activation and audio recitation functions are generally programmable and operable on industry standard smart devices, such as various device models of iPhone, iPad, Samsung Galaxy, HP tablets, Google glass, iWatch, etc, running on operating systems such as Android, iOS, and Windows, where such devices include an accelerometer. Any such mobile device having the minimum function set as described herein is anticipated. Implementation using on-board devices installed as vehicle equipment is also anticipated.

Preferred embodiments of the present invention may comprise generating personalized adjustment parameters directed to positioning and control of seating configurations in furniture, including tilt and recline angle, seat and back shape, firmness and support. Outcome objectives may reflect both safety and comfort. A smartphone implementation providing a user interface to display at least current position and shape parameters and send related control parameters to powered, adjustable seats is anticipated. System responses are anticipated to at least user touch and voice commands. Audio recitation and response is anticipated. User touch, voice activation and audio recitation functions are generally programmable and operable on industry standard smart devices, such as various device models of iPhone, iPad, Samsung Galaxy, HP tablets, Google glass, iWatch, etc., running on operating systems such as Android, iOS, and Windows, where such devices include an accelerometer. Any such mobile device having the minimum function set as described herein is anticipated. Implementation using on-board devices installed as furniture components is also anticipated.

Preferred embodiments of the present invention may comprise generating personalized adjustment parameters directed to positioning and control of support and comfort configurations in both commercial and private sleep platforms for healthcare, hospitality and in-home applications. A smartphone implementation providing a user interface to display at least current position and shape parameters, and send related control parameters to powered, adjustable seats is anticipated. System responses are anticipated to at least user touch and voice commands. Audio recitation and response is anticipated. User touch, voice activation and audio recitation functions are generally programmable and operable on industry standard smart devices, such as various device models of iPhone, iPad, Samsung Galaxy, HP tablets, Google glass, iWatch, etc., running on operating systems such as Android, iOS, and Windows. Any such mobile device having the minimum function set as described herein is anticipated. Implementation using on-board devices installed as sleep-platform equipment components is also anticipated.

Preferred embodiments of the present invention may comprise using the goniometer functions implemented in a mobile device for generating and recording personalized parameters directed to measuring and scoring joint range of motion and flexibility by clinicians including at least physical therapists, orthopedists, physical medicine clinicians and sports medicine practitioners. Goniometric measurements provided using the mobile version of the present invention may be used as outcome measures (e.g., after a course of treatment), as an exam finding to aid in the diagnosis of a condition, and to determine level of fitness for a specific purpose. System responses are anticipated to at least user touch and voice commands. Audio recitation and response is anticipated. User touch, voice activation and audio recitation functions are generally programmable and operable on industry standard smart devices, such as various device models of iPhone, iPad, Samsung Galaxy, HP tablets, Google glass, iWatch, etc., running on operating systems such as Android, iOS, and Windows. Any such mobile device having the minimum function set as described herein is anticipated.

Those skilled in the art will appreciate that in some embodiments of the invention, the functional modules of the Web implementation, as well as the personal and the integrated communication devices, may be implemented as pre-programmed hardware or firmware elements (e.g., application specific integrated circuits (ASICs), electrically erasable programmable read-only memories (EEPROMs), etc.), or other related components. Mobile communication devices that can use the present invention may include but are not limited to any of the "smart" phones or tablet computers equipped with digital displays, wireless communication connection capabilities such as iPhones and iPads available from Apple, Inc., as well as communication devices configured with the Android operating system available from Google, Inc and with the Windows operating system available from Microsoft. In addition, it is anticipated that the new communication devices and operating systems will become available as more capable replacements of the forgoing listed communication devices, and these may use the present invention as well.

In other embodiments, the functional modules of the mobile-to-cloud implementation may be implemented by an arithmetic and logic unit (ALU) having access to a code memory which holds program instructions for the operation of the ALU. The program instructions could be stored on a medium which is fixed, tangible and readable directly by the processor, (e.g., removable diskette, CD-ROM, ROM, or fixed disk), or the program instructions could be stored remotely but transmittable to the processor via a modem or other interface device (e.g., a communication adapter) connected to a network over a transmission medium. The transmission medium may be either a tangible medium (e.g., optical or analog communications lines) or a medium implemented using wireless techniques (e.g., microwave, infrared or other transmission schemes).

The program instructions stored in the code memory can be compiled from a high level program written in a number of programming languages for use with many computer architectures or operating systems. For example, the program may be written in assembly language suitable for use with a pixel shader, while other versions may be written in a procedural programming language (e.g., "C") or an object oriented programming language (e.g., "C++" or "JAVA").

In other embodiments, cloud computing may be implemented on a web hosted machine or a virtual machine. A web host can have anywhere from one to several thousand computers (machines) that run web hosting software, such as Apache, OS X Server, or Windows Server. A virtual machine (VM) is an environment, usually a program or operating system, which does not physically exist but is created within another environment (e.g., Java runtime). In this context, a VM is called a "guest" while the environment it runs within is called a "host." Virtual machines are often created to execute an instruction set different than that of the host environment. One host environment can often run multiple VMs at once.

While specific embodiments of the present invention have been described and illustrated, it will be apparent to those skilled in the art that numerous modifications and variations can be made without departing from the scope of the invention as defined in the appended claims. It is understood that the words that have been used are words of description and illustration, rather than words of limitation. Although the invention has been described with reference to particular means, materials and embodiments, the invention is not intended to be limited to the particulars disclosed; rather, the invention extends to all functionally equivalent structures, methods and uses, such as are within the scope of the appended claims.

I claim:

1. A method for providing personalized configuration of a sleep platform for the human body, comprising:
    providing an artificial neural network having a layered network structure in which processing units (i.e., neurons) are arranged in layers, where the neurons in adjacent layers can communicate with each other by sending and receiving signals through weighted connections;
    accepting input including demographic information, neurological attributes, physical history, operational environment, and outcome or use objectives for at least one individual, and operating said artificial neural network to transform said input into quantified parameters usable for adjusting angular position of said sleep platform personalized for said at least one individual;
    returning said quantified parameters including at least one of guidance and control parameters directed to adjustment of at least one of support and comfort configurations in said sleep platform;
    providing actionable aural guidance recounted using an electronic device said aural guidance directed to adjusting said angular position of said sleep platform in substantially real-time;
    providing a goniometer operating in a mobile device adapted to determine initial spatial orientation of said mobile device and to enable substantially accurate measurement of changes in said spatial orientation relative to any physical orientation in which said mobile device is positioned;
    altering angular positioning of said sleep platform in accordance with said guidance and control parameters;
    measuring using said goniometer changes in said angular positioning with respect to said initial spatial orientation of said mobile device, and
    ceasing alteration of said angular positioning upon compliance with said guidance.

2. The method of claim 1 further comprising, providing said mobile device removably mountable on said sleep platform, adapted to at least collect user information, request guidance on position parameters of said sleep platform, display results, and receive orientation data produced to measure at least tilt and recline angles of said sleep platform.

3. The method of claim 1 wherein, said artificial intelligence network is included in an artificial intelligence module adapted to operate in an Internet cloud computing environment.

4. The method of claim 1, wherein behavior of a neuron in said artificial neural network is defined by its internal activation function, which accumulates input signals and then calculates outputs, and wherein a learning process proceeds in iterations by tuning weights of connections using a training algorithm.

5. The method of claim 1, wherein the method is implemented as a specific purpose mobile device comprising a computational framework, artificial neural network, a goniometer, and controls for positioning and adjustment settings directed to providing position and shape control parameters for said sleep platform.

6. The method of claim 1, wherein said artificial neural network is embodied as an artificial intelligence (AI) module trained with clinical research data directed to optimal positioning and adjustment of said sleep platform for a defined purpose or desired outcome.

7. The method of claim 1, wherein users input into a user interface demographic, neurological, and pressure ulcer history information for an individual.

8. The method of claim 1, wherein said artificial neural network is replaced by an alternative artificial intelligence technique, comprising any one of a classification, clustering, or regression technique.

9. A system for providing personalized configuration of a sleep platform for the human body, comprising:
a user interface for accepting input including at least one of demographic information, neurological attributes, physical history, operational environment, and outcome or use objectives for at least one individual;
an artificial intelligence module adapted to operate in an Internet cloud said artificial intelligence module adapted to transform said input into quantified parameters usable for adjusting angular position of said sleep platform personalized for said at least one individual;
an artificial neural network (ANN) having a layered network structure, in which processing units (i.e., neurons) are arranged in layers, where the neurons in adjacent layers can communicate with each other by sending and receiving signals through weighted connections;
a mobile device adapted to at least collect user information, request guidance on support position parameters, display results, and receive input captured by an angle measuring device;
wherein said mobile device is adapted to provide actionable aural guidance directed to achieving said quantified parameters in substantially real-time;
wherein a goniometer operating in said mobile device is adapted to determine initial spatial orientation of said mobile device and enable substantially accurate measurement of changes in sleep platform position angles relative to any physical orientation in which said mobile device is positioned on said sleep platform,
wherein said quantified parameters are provided to direct positioning and control of at least one of support and comfort configurations in said sleep platform for at least one of healthcare, hospitality, and in-home applications,
wherein angular positioning of said sleep platform is adjusted in accordance with said quantified parameters; and
wherein said goniometer measures changes in said position angles with respect to said initial spatial orientation of said mobile device.

10. The system of claim 9, further comprising a specific purpose device integrated into a powered sleep platform, where the device includes a computational framework, said artificial neural network, said goniometer, and a controller operational for actuating adjustment of at least angular position in said sleep platform and ceasing said adjustment when said at least angular position has achieved said quantified parameters.

11. The system of claim 9, wherein said goniometer is adapted to measure at least current physical position angles and contrast those angles with guidance angles to generate control parameters that cause angular position of a powered sleep platform to be altered.

12. The system of claim 11, further comprising a user interface adapted to display at least shape and angular position parameters for said sleep platform.

13. The system of claim 12, wherein further comprising a communication module adapted to output wirelessly a control function operating in a powered sleep platform to adjust at least one of shape and angular orientation of said powered sleep platform.

14. The system of claim 12, wherein said goniometer includes an accelerometer sensor configured in said mobile device to measure angles relative to any physical orientation in which said mobile device is positioned.

15. The system of claim 9, wherein a user registration component is provided which allows users to create and review profiles comprising at least one of demographic information, neurological information, and pressure ulcer history.

16. The system of claim 10, wherein said quantified parameters are applied by said controller to achieve favorable pressure reduction for an intended occupant of said sleep platform, at least optimal shape, tilt and recline angles that are most effective in reducing the risk of pressure ulcers, and optimal frequency and duration of said adjustment to sleep platform reconfiguration.

17. An apparatus for determining optimal positioning for a sleep platform support orientation, comprising:
a user interface on a mobile device that accepts input including demographic information, neurological attributes, and injury history for at least one individual, said mobile device adapted to at least collect user information, request guidance on sleep platform angular position parameters, display results to the user, and receive input captured by a goniometer to measure sleep platform orientation angles;
an artificial intelligence engine that provides at least one of guidance and control parameters directed to at least: (1) favorable sleep platform angular settings; (2) optimal sleep platform position angles that may most effectively reduce pressure ulcer risks; (3) optimal duration and frequency to perform sleep platform reconfiguration functions; and (4) measurement of position angles by implementing said goniometer;
an artificial intelligence module operable in an Internet cloud, including an artificial neural network (ANN) having a layered network structure, in which processing units (i.e., neurons) are arranged in layers, the neurons in adjacent layers adapted to communicate with each other by sending and receiving signals through weighted connections;

wherein said artificial intelligence module is adapted to receive said input from said mobile device and transform said input into quantified parameters usable for adjusting angular position of said sleep platform personalized for said at least one individual;

wherein said mobile device is adapted to provide actionable aural guidance directed to achieving said quantified parameters in substantially real-time as position-settings are adjusted on said sleep platform;

wherein a goniometer operating in said mobile device is adapted to determine spatial orientation of said mobile device and enable substantially accurate measurement of changes in angles relative to any physical orientation in which said mobile device is positioned on said sleep platform, wherein said personalized parameters are provided to direct positioning and control of support and comfort configurations in said sleep platform for at least one of healthcare, hospitality, and in-home applications, wherein angular positioning of said sleep platform is adjusted in accordance with said quantified parameters; and wherein said goniometer measures changes in said position angles with respect to said initial spatial orientation of said mobile device, and wherein alteration of said angular positioning is halted upon compliance with said guidance.

18. The apparatus of claim 17, wherein said goniometer can work independently or in conjunction with said artificial intelligence engine.

19. The apparatus of claim 17, wherein said sleep platform is one of a manual sleep platform or a power sleep platform.

* * * * *